US009265735B2

(12) United States Patent
Nixon et al.

(10) Patent No.: US 9,265,735 B2
(45) Date of Patent: Feb. 23, 2016

(54) METHODS FOR SCREENING TO IDENTIFY THERAPEUTIC AGENTS FOR ALZHEIMER'S DISEASE AND USE THEREOF

(75) Inventors: Ralph A. Nixon, Tarrytown, NY (US); Ju-Hyun Lee, Cresskill, NJ (US); Devin Wolfe, Airmont, NY (US)

(73) Assignees: New York University, New York, NY (US); The Research Foundation for Mental Hygiene, Inc., Menands, NY (US)

(*) Notice: Subject to any disclaimer, the term of this patent is extended or adjusted under 35 U.S.C. 154(b) by 56 days.

(21) Appl. No.: 13/307,485

(22) Filed: Nov. 30, 2011

(65) Prior Publication Data

US 2012/0136064 A1    May 31, 2012

Related U.S. Application Data

(60) Provisional application No. 61/458,687, filed on Nov. 30, 2010.

(51) Int. Cl.
*A61K 31/137* (2006.01)
*A61K 31/00* (2006.01)
*C12Q 1/37* (2006.01)

(52) U.S. Cl.
CPC .............. *A61K 31/00* (2013.01); *A61K 31/137* (2013.01); *C12Q 1/37* (2013.01); *G01N 2333/96466* (2013.01); *G01N 2333/96472* (2013.01); *G01N 2500/10* (2013.01); *G01N 2800/2821* (2013.01)

(58) Field of Classification Search
None
See application file for complete search history.

(56) References Cited

U.S. PATENT DOCUMENTS

| 7,951,367 | B2 | 5/2011 | Gan et al. |
| 8,067,183 | B2 | 11/2011 | Shapiro |
| 2008/0160008 | A1 | 7/2008 | Gan et al. |
| 2011/0256120 | A1 | 10/2011 | Gan et al. |
| 2012/0052053 | A1* | 3/2012 | Manning-Bog et al. ... 424/94.61 |
| 2013/0096126 | A1* | 4/2013 | Shamloo ............. A61K 31/137 514/237.5 |

FOREIGN PATENT DOCUMENTS

| WO | 03020257 | 3/2003 |
| WO | 2006082046 | 8/2006 |

OTHER PUBLICATIONS

Bjorkoy et al., "p62/SQSTM1 forms protein aggregates degraded by autophagy and has a protective effect on huntingtin-induced cell death", J Cell Biol, 2005, 171, 603-614.
Boland et al., "Autophagy induction and autophagosome clearance in neurons: Relationship to autophagic pathology in Alzheimer's Disease", J Neurosci, 2008, 28, 6926-6937.

(Continued)

*Primary Examiner* — Svetlana M Ivanova
(74) *Attorney, Agent, or Firm* — Klauber & Jackson LLC

(57) ABSTRACT

Methods for treating Alzheimer's Disease (AD) using modulators of lysosomal activity are described herein. More particularly, methods described herein relate to the use and application of compounds or agents that enhance lysosomal activity for the treatment of AD. In a particular aspect, the method relates to the use and application of compounds or agents that increase the pH of the lysosome and/or increase the overall activity of lysosomal proteases for the treatment of AD. Also described herein are methods and assays for screening to identify compounds or agents that increase the pH of the lysosome and/or increase the overall activity of lysosomal proteases for the treatment of AD.

15 Claims, 16 Drawing Sheets

(56) References Cited

OTHER PUBLICATIONS

Cataldo et al., "Presenilin mutations in familial Alzheimer Disease and transgenic mouse models accelerate neuronal lysosomal pathology", J Neuropathol Exp Neurol, 2004, 63, 821-830.

Cuervo et al., "Impaired degradation of mutant α-synuclein by chaperone-mediated autophagy", Science, 2004, 305, 1292-1295.

De Strooper et al., "Deficiency of presenilin-1 inhibits the normal cleavage of amyloid precursor protein", Nature, 1998, 391, 387-390.

Esselens et al., "Presenilin 1 mediates the turnover of telencephalin in hippocampal neurons via an autophagic degradative pathway", J Cell Biol, 2004, 166, 1041-1054.

Hara et al., "Suppression of basal autophagy in neural cells causes neurodegenerative disease in mice", Nature, 2006, 441, 885-889.

Shioi et al., "FAD mutants unable to increase neurotoxic Aβ42 suggest that mutation effects on neurodegeneration may be independent of effects on Aβ", Journal of Neurochemistry, 2007, 101, 674-681.

Kokkonen et al., "Defective acidification of intracellular organelles results in aberrant secretion of cathepsin D in cancer cells", J Biol Chem, 2004, 279, 39982-39988.

Komatsu et al., "Loss of autophagy in the central nervous system causes neurodegeneration in mice", Nature, 2006, 441, 880-884.

Nixon et al., "Extensive involvement of autophagy in Alzheimer Disease: An Immuno-Electron Microscopy Study", J Neuropathol Exp Neurol, 2005, 64, 113-122.

Ravikumar et al., "Inhibition of mTOR induces autophagy and reduces toxicity of polyglutamine expansions in fly and mouse models of Huntington Disease", Nat Genet, 2004, 36, 585,595.

Yamamoto et al., "Bafilomycin A1 prevents maturation of autophagic vacuoles by inhibiting fusion between autophagosomes and lysosomes in rat hepatoma cell line, H-4-II-E cells", Cell Struct Funct, 1998, 23, 33-42.

Yoshimori et al., "Bafilomycin A1, a specific inhibitor of vacuolar-type H(+)-ATPase, inhibits acidification and protein degradation in lysosomes of cultured cells", J Biol Chem, 1991, 266, 17707-17712.

Yu et al., "Macroautophagy—a novel β-amyloid peptide-generating pathway activated in Alzheimer's Disease", J Cell Biol, 2005, 171, 87-98.

Saber et al., "Combined beta-adrenergic and cholinergic antagonism produces behavioral and cognitive impairments in the water made: Impolications for Alzheimer Disease and pharmacotherapy with beta-adrenergic antagonists", Neuropsychopharmacology, 2003, 28, 1247-1256.

Liu et al., "Restoration of lysosomal ph in RPE cells from cultured human and ABCA4-/- mice: Pharmacologic approaches and functoinal recovery", Invest Opthalmol Vis Sci, 2008, 49, 772-780.

Gibbs et al., "Memory loss caused by beta-amyloid protein is rescued by a beta3-adrenoceptor agonist", Neurobiology of Aging, 2010, 614-624.

Sun et al., "Cystatin C-cathepsin B axis regulates amyloid beta levels and associated neuronal deficits in an animal model of Alzheimer's Disease", Neuron, 2008, 60, 247-257.

Huang et al., "Altered beta-adrenergic receptor-stimulated cAMP formation in cultured skin fibroblasts rom alzheimer donors", The Journal of Biological Chemistry, 268, 14616-14621.

Hook et al., "Pharmacogenetic features of cathepsin beta inhibitors that improve memory deficit and reduce beta amyloid related to Alzheimer's Disease", Biol Chem, 2010, 391, 861-872.

Butler et al., "Protective effects of positive lysosomal modulation in Alzheimer's Disease transgenic mouse models", PLoS One, 2011, 6, e20501.

Gleeson et al., "The beta2-adrenoceptor agonist clenbuterol elicits neuroprotective, anti-inflammatory and neurotrophic actions in the kainic acid model and excitotoxicity", Brain, Behavior and Immunity, 2010, 24, 1354-1361.

Culmsee et al., "Combination therapy in ischemic stroke: synergistic neuroprotective effects of memantine and clenbuterol", Stroke, 2004, 35, 1197-1202.

Wolfe et al., "Alzheimer protease hitches a ride", Nature Medicine, 2006, 12, 1352.

Sun et al., "Bilateral injection of isoproterenol into hippocampus induces Alzheimer-like hyperphosphorylation of tau and spatial memory deficit in rat", FEBS Letters, 2005, 579, 251-258.

Cole et al., "Cat and mouse", Neuron, 2006, 51, 671-684.

Lee et al., "Lysosomal proteolysis and autophagy require presenilin 1 and are disrupted by Alzheimer-related PS1 mutations", Cell, 2010, 141, 1146-1158.

Schwagerl et al., "Elevated levels of the endosomal-lysosomal proteinase cathepsin D in cerebrospinal fluid in Alzheimer Disease", Journal of Neurochemistry, 1995, 64, 443-446.

Mueller-Seiner et al., "Antiamyloidogenic and neuroprotective functions of cathepsin B: implications for Alzheimer's Disease", Neuron, 51, 703-714.

Nixon et al., "Lysosomal system pathways: Genes to neurodegeration in Alzheimer's Disease", Journal of Alzheimer's Disease, 2006, 9, 277-289.

Zhang et al., "The lysosome and neurodegerative diseases", ABBS, 2009, 41, 437-435.

Urbanelli et al., "Cathepsin D expression is decreased in Alzheimer's Disease fibroblasts", Neurobiol Aging, 2008, 29, 12-22.

Bahr et al., "Induction of beta-amyloid-containing polypeptides in hippocampus: evidence ofr a concomitant loss of synaptic proteins and interactions with an excitotoxin", Experimental Neurology, 1994, 129, 81-94.

Nixon et al., "The endosomal-lysosomal system of neurons in Alzheimer's Disease pathogenesis: A review", Neurochemical Research, 2000, Sep. 2010, 1161-1172.

Cataldo et al., "Lysosomal proteinase antigens are prominently localized within senile plaques of Alzheimer's disease: evidence for a neuronal origin", Brain Research, 1990, 513: 181-192.

Liao et al., "Proteomic characterization of postmortem amyloid plaques isolated by laser capture microdissection", J Biol Chem, 2004, 279:37061-37068.

Xia et al., "Proteomic identification of novel proteins associated with Lewy bodies", Front Biosci, 2008, 13:3850-3856.

Wei et al., "Enhanced lysosomal pathology caused by beta-synuclein mutants linked to dementia and Lewy bodies", J Biol Chem, 2007, 282:28904-28914.

Bisaglia et al., "Structure and topology of the non-amyloid-beta component fragment of human alpha-synuclein bound to micelles: Implications for the aggregation process", Protein Science, 2006, 15:1408-1416.

McKeith et al., "Dementia with Lewy bodies", in Neuropsychopharmacology: The Fifth Generation of Progress, K. L. Davis et al., (eds), New York, 2002.

Chung et al., "Alzheimer's disease and Parkinson's disease genome-wide association study top hits and risk of Parkinson's disease in Korean population", Neurobiol of Aging, 2013, 34:2695.e1-2695.e7.

Kurzawa-Akanbi et al., "Glucocerebrosidase mutations alter the endoplasmic reticulum and lysosomes in Lewy body disease", J Neurochem, 2012, 123:298-309.

Muangpaisan, "Clinical differences among four common dementia syndromes", Geriatrics and Aging, 2007, 10:425-429.

Chang et al, "Parkinson's and Alzheimer's diseases: similar but very different", http://www.alznyc.org/nyc/newsletter/fall2012/06.asp#.VBHczfldXec0, 2012.

Cataldo et al., "Increased neuronal endocytosis and protease delivery to early endosomes in sporadic Alzheimer's disease: neuropathologic evidence for a mechanism of increased beta-amyloidogenesis", J Neurosci., 1997, 17:6142-51.

Cataldo et al., "Endocytic pathway abnormalities precede amyloid beta deposition in sporadic Alzheimer's disease and Down syndrome: differential effects of APOE genotype and presenilin mutations", Am J Pathol, 2000, 157:277-86.

Cataldo et al., "App gene dosage modulates endosomal abnormalities of Alzheimer's disease in a segmental trisomy 16 mouse model of down syndrome", J Neurosci., 2003, 23:6788-92.

Cataldo et al., "Down syndrome fibroblast model of Alzheimer-related endosome pathology: accelerated endocytosis promotes late endocytic defects", Am J Pathol., 2008, 173:370-84.

Ginsberg et al., "Microarray analysis of hippocampal CA1 neurons implicates early endosomal dysfunction during Alzheimer's disease progression", Biol Psychiatry, 2010, 68:885-93.

(56) References Cited

OTHER PUBLICATIONS

Grbovic et al., "Rab5-stimulated up-regulation of the endocytic pathway increases intracellular beta-cleaved amyloid precursor protein carboxyl-terminal fragment levels and Abeta production", J Biol Chem., 2003, 278:31261-8.

Hooli et al., "Role of common and rare APP DNA sequence variants in Alzheimer disease", Neurology, 2012, 78:1250-7.

Israel et al., "Probing sporadic and familial Alzheimer's disease using induced pluripotent stem cells", Nature 2012; 482: 216-220.

Jiang et al., "Alzheimer's-related endosome dysfunction in Down syndrome is Abeta-independent but requires APP and is reversed by BACE-1 inhibition", Proc Natl Acad Sci U S A., 2010, 107:1630-5.

Kim et al., "Evidence that the rab5 effector APPL1 mediates APP-βCTF-induced dysfunction of endosomes in Down syndrome and Alzheimer's disease", Mol Psychiatry, 2015, 1-10.

Salehi et al., "Increased App expression in a mouse model of Down's syndrome disrupts NGF transport and causes cholinergic neuron degeneration", Neuron, 2006, 51:29-42.

Vassar, "BACE1 inhibitor drugs in clinical trials for Alzheimer's disease", Alzheimers Res Ther, 2014, 6:89, 1-14.

* cited by examiner

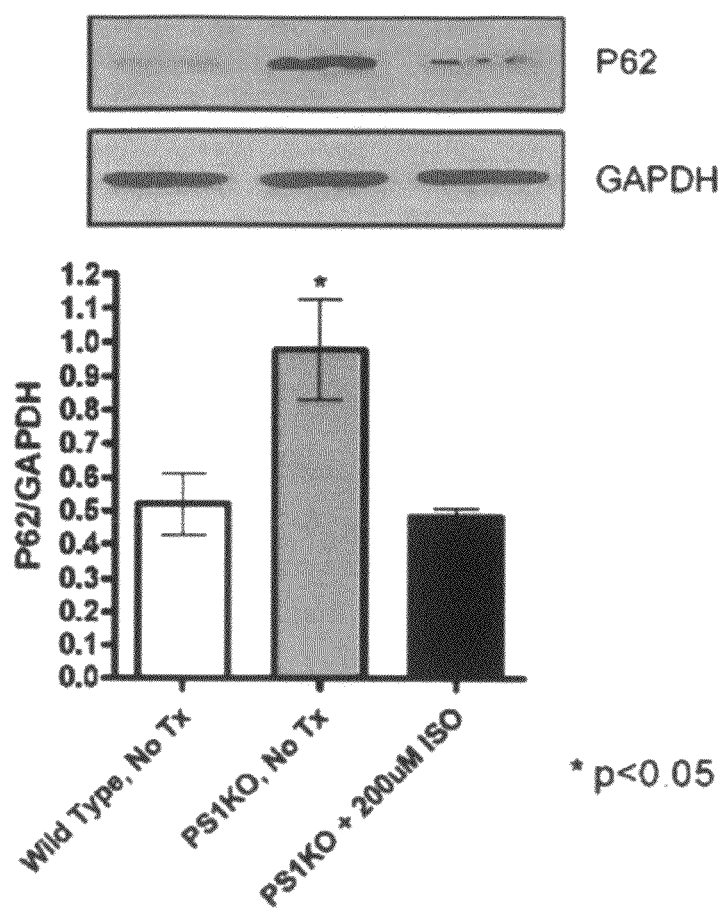

METHODS FOR SCREENING TO IDENTIFY THERAPEUTIC AGENTS FOR ALZHEIMER'S DISEASE AND USE THEREOF

CROSS REFERENCE TO RELATED APPLICATION

This application claims priority under 35 USC §119(e) from U.S. Provisional Application Ser. No. 61/458,687, filed Nov. 30, 2010, which application is herein specifically incorporated by reference in its entirety.

GOVERNMENT SUPPORT

The research leading to the present invention was funded in part by National Institutes of Health grant AG017617. The United States government has certain rights in the invention.

FIELD OF THE INVENTION

The present invention relates generally to the treatment of Alzheimer's Disease (AD). More particularly, the present invention relates generally to the treatment of AD using modulators of lysosomal activity. Accordingly, the invention relates to the use and application of compounds or agents that enhance lysosomal activity for the treatment of AD. In a particular aspect, the invention relates to the use and application of compounds or agents that increase the pH of the lysosome and/or that increase the overall activity of lysosomal proteases for the treatment of AD. The present invention also relates to methods and assays for screening to identify compounds or agents that increase the pH of the lysosome and/or that increase the overall activity of lysosomal proteases for the treatment of AD.

BACKGROUND OF THE INVENTION

Macroautophagy, the major lysosomal degradative pathway in cells, is responsible for degrading long-lived cytoplasmic constituents and is the principal mechanism for turning over cellular organelles and protein aggregates too large to be degraded by the proteasome (Klionsky, 2007; Mizushima, 2007; Rubinsztein, 2006). When macroautophagy is genetically ablated, neurons accumulate ubiquitinated protein aggregates and degenerate (Hara et al., 2006; Komatsu et al., 2006).

Macroautophagy, hereafter referred to as autophagy, involves the sequestration of a region of cytoplasm within an enveloping double-membrane structure to form an autophagosome. Autophagosome formation is induced by inhibition of mTOR (mammalian target of Rapamycin), a protein kinase modulated by signaling pathways involving either class I phosphatidylinositol-3-kinase (PI3K)-Akt/protein kinase B (PKB) (Schmelzle and Hall, 2000) or AMP-activated protein kinase (AMPK) (Samari and Seglen, 1998). Autophagosomes and their contents are cleared upon fusing with late endosomes or lysosomes that contain cathepsins, other acid hydrolases, and vacuolar [$H^+$] ATPase (v-ATPase) (Yamamoto et al., 1998), a proton pump that acidifies the newly created autolysosome. Acidification of autolysosomes is crucial for activating cathepsins and effecting proteolysis of substrates; however, these late digestive steps of autophagy remain relatively uncharacterized.

Autophagic vacuoles (AVs), the general term for intermediate vesicular compartments in the process of autophagy, accumulate in several neurodegenerative diseases including Alzheimer's disease (AD), Parkinson's disease, and Huntington disease (Cuervo et al., 2004; Nixon et al., 2005; Ravikumar et al., 2004). Autophagy pathology is exceptionally robust in AD, where AVs collect in massive numbers within grossly distended portions of axons and dendrites of affected neurons (Yu et al., 2005), likely reflecting defective AV clearance (Boland et al., 2008). This lysosome-related pathology, along with neuronal loss and amyloid deposition, are greatly accentuated in early-onset familial AD (FAD) due to mutations of PS1, the most common cause of FAD (Cataldo et al., 2004).

Presenilin-1 (PS1), a ubiquitous transmembrane protein, has diverse putative biological roles in cell adhesion, apoptosis, neurite outgrowth, calcium homeostasis, and synaptic plasticity (Kim and Tanzi, 1997; Shen and Kelleher, 2007). PS1 holoprotein, a ~45 kDa protein, is cleaved in the endoplasmic reticulum (ER) to create a heterodimer (Zhang et al., 1998). Many known PS1 functions, but not all, involve the cleaved heterodimeric form of PS1 as the catalytic subunit of the gamma ($\gamma$)-secretase enzyme complex, which mediates the intramembranous cleavage of many type 1 membrane proteins, including APP and Notch (Citron et al., 1997; De Strooper et al., 1998). Although the pathogenic effects of PS1 mutations in AD are commonly ascribed to increased generation of the neurotoxic A$\beta$ peptide from APP, not all of the disease-causing PS1 mutations have this effect (Junichi et al., 2007). Additional contributions to AD pathogenesis may involve loss of one or more of the other suspected biological functions of PS1, which include the roles described above and the trafficking or turnover of transmembrane proteins (Naruse et al., 1998).

The underlying causes of AD are not understood. It is to this objective of better defining the mechanistic underpinnings of AD etiology and/or progression that the present results are directed. An appreciation of the biochemical and cellular mechanisms that contribute to AD, in turn, imparts guidance that can be applied to the development and testing of therapeutics for the treatment of AD patients.

The citation of references herein shall not be construed as an admission that such is prior art to the present invention.

SUMMARY OF THE INVENTION

As described herein, the present inventors show that PS1 is required for lysosomal turnover of autophagic and endocytic protein substrates. PS1 deletion causes complete loss of macroautophagy while having minimal influence on non-lysosomal types of proteolysis. We have identified the molecular basis for this requirement to be a novel action of PS1 holoprotein in the ER as an ER chaperone to facilitate maturation and targeting of the v-ATPase V0a1 subunit to autolysosomes, which is essential for acidification, protease activation, and degradation of autophagic/lysosomal substrates. We demonstrate defects in these processes in cells lacking PS1, which are completely reversed by introducing wild type human PS1 into the cells. Similar autophagy pathology and deficits in lysosomal acidification are demonstrated in neurons of mice hypomorphic for PS1 or conditional PS knockout mice. Of particular clinical significance, we further show that mutations of PS1 that cause early-onset familial AD (FAD) disrupt the same lysosomal/autophagic functions that are more severely affected in PS1 KO cells. Our findings underscore the pathogenic importance of lysosomal proteolytic dysfunction seen in all forms of AD (Nixon and Cataldo, 2006; Nixon 2008) and provide a basis for the accelerated autophagy dysfunction and defective neuronal protein clearance seen in PS-FAD, which is associated with early onset of AD.

In its broadest aspect, the present invention encompasses enhancing lysosomal activity in a mammal, particularly in a human, afflicted with a condition or disease wherein impaired lysosomal activity is associated with the condition or disease, by administering an agent or compound that enhances lysosomal activity in the mammal. The invention also encompasses use an agent or compound that enhances lysosomal for treating a condition or disease associated with impaired lysosomal activity. In a particular aspect, the present invention extends to the treatment of AD in mammals, particularly in humans, using agents or compounds that enhance lysosomal activity.

Accordingly, a method for treating a subject with AD, wherein the subject has impaired lysosomal activity is described herein, the method comprising administering to the subject an agent that enhances lysosomal activity.

In an embodiment thereof, the impaired lysosomal activity is determined by measuring elevated pH levels in lysosomes of the subject.

In a particular embodiment, the elevated pH level in lysosomes is equal to or greater than about 5.2.

In an aspect of the method, the impaired lysosomal activity is determined before, concurrently, or after the administering of the agent to the subject. In a particular embodiment thereof, the impaired lysosomal activity is determined before and after the administering of the agent to the subject. In another embodiment thereof, the impaired lysosomal activity is determined before or after the administering of the agent to the subject.

In a further aspect, the impaired lysosomal activity is determined by detecting reduced levels of lysosomal protease activity in cells of the subject. In a particular aspect, the reduced levels of lysosomal protease activity reflect a general or overall reduced activity level of essentially all or nearly all of the lysosomal proteases. The reduced levels of lysosomal protease activity observed in the cells of the subject are, therefore, not due to reduced levels of activity for a specific lysosomal protease.

In a particular embodiment thereof, the reduced levels of lysosomal protease activity in cells of the subject is associated with reduced activity of at least three lysosomal proteases.

In another particular embodiment, the impaired lysosomal activity is determined using a sample isolated from the subject before and after the administering of the agent to the subject. In yet another particular embodiment, the impaired lysosomal activity is determined using a sample isolated from the subject before or after the administering of the agent to the subject.

In an aspect thereof, the isolated sample comprises or is skin fibroblasts, lymphocytes or other white cell subtypes, particularly with respect to assays pertaining to lysosomal pH or other lysosomal functions. For assays of cathepsin D (catD) specific activity: blood plasma or serum, urine, saliva, and cell samples such as, for example, skin fibroblasts, lymphocytes or other white cell subtypes, could be assayed for catD alterations. In a particular embodiment, the sample is cerebrospinal fluid isolated from the subject. In an embodiment thereof, the cerebrospinal fluid is lumbar cerebrospinal fluid.

In an aspect of the method, the agent is a β-adrenergic agonist, a cAMP agonist, a Ca2+ pump inhibitor, a phosphodiesterase inhibitor, a chloride channel activator, an L-type calcium channel blocker, a purinergic agent, an anti-oxidant, a cAMP-activated protein kinase inhibitor, a cathepsin activator, a sirtuin activator, a lipofuscinolytic, a ceroid depletor, an imidazole-1 receptor agonist, a calpain inhibitor, or an anti-lipolytic agent.

In a particular aspect thereof, wherein the agent is a β-adrenergic agonist, cAMP agonist, Ca2+ pump inhibitor, or a phosphodiesterase inhibitor.

In a more particular aspect, the agent is isoproterenol or a derivative thereof.

In another particular aspect thereof, the agent is clenbuterol or a derivative thereof.

In a particular embodiment, the subject is a mammal. In a more particular embodiment, the subject is a human.

Also encompassed herein is use of an agent that enhances lysosomal activity for treating AD, whereby the agent enhances lysosomal activity, thereby treating the AD. In an embodiment thereof, the impaired lysosomal activity is determined by measuring elevated pH levels in lysosomes of the subject. In a particular embodiment, the elevated pH level in lysosomes is equal to or greater than about 5.2. The impaired lysosomal activity can be determined before, concurrently, or after use of the agent or, more particularly, the impaired lysosomal activity can be determined before and after use of the agent to the subject, or before or after use of the agent to the subject. In a further aspect, the impaired lysosomal activity is determined by detecting reduced levels of lysosomal protease activity in cells of the subject. The reduced levels of lysosomal protease activity reflect a general or overall reduced activity level of essentially all or nearly all of the lysosomal proteases. The reduced levels of lysosomal protease activity observed in the cells of the subject are, therefore, not due to reduced levels of activity for a specific lysosomal protease. The reduced level of lysosomal protease activity in cells of the subject is associated with reduced activity of at least three lysosomal proteases. In a further embodiment, the impaired lysosomal activity is determined using a sample isolated from a subject before and after the use of the agent. In yet another particular embodiment, the impaired lysosomal activity is determined using a sample isolated from the subject before or after using the agent. The isolated sample may comprise or consist of skin fibroblasts, lymphocytes or other white cell subtypes, particularly with respect to assays pertaining to lysosomal pH or other lysosomal functions. For assays of cathepsin D (catD) specific activity: blood plasma or serum, urine, saliva, and cell samples such as, for example, skin fibroblasts, lymphocytes or other white cell subtypes, could be assayed for catD alterations. In a particular embodiment, the sample is cerebrospinal fluid isolated from the subject. In an embodiment thereof, the cerebrospinal fluid is lumbar cerebrospinal fluid. In an aspect thereof, the agent is a β-adrenergic agonist, a cAMP agonist, a Ca2+ pump inhibitor, a phosphodiesterase inhibitor, a chloride channel activator, an L-type calcium channel blocker, a purinergic agent, an anti-oxidant, a cAMP-activated protein kinase inhibitor, a cathepsin activator, a sirtuin activator, a lipofuscinolytic, a ceroid depletor, an imidazole-1 receptor agonist, a calpain inhibitor, or an anti-lipolytic agent. More particularly, the agent is a β-adrenergic agonist, cAMP agonist, Ca2+ pump inhibitor, or a phosphodiesterase inhibitor. Even more particularly, the agent is isoproterenol or a derivative thereof or clenbuterol or a derivative thereof.

Also encompassed herein is a method for screening potential compounds or agents to identify a compound or agent that enhances lysosomal activity, the method comprising contacting a population of cells, wherein the cells have impaired lysosomal activity detectable by elevated lysosomal pH or reduced activity of at least three lysosomal proteases, with at least one potential compound or agent and assessing the ability of the at least one potential compound or agent to enhance lysosomal activity in the cells of the population, wherein if contact with the at least one potential compound or agent enhances lysosomal activity relative to contact with a control compound or agent, the at least one potential compound or agent is identified as compound or agent that enhances lysosomal activity.

In a particular embodiment of the screening assay, the population of cells is isolated from a subject with Alzheimer's Disease (AD).

In a particular embodiment of the screening assay, wherein the elevated pH is equal to or greater than about 5.2.

In another particular embodiment of the screening assay, the at least three lysosomal proteases having reduced activity are selected from the group consisting of Cathepsin B (catB), Cathepsin D (catD), and Cathepsin L (catL).

Other objects and advantages will become apparent to those skilled in the art from a review of the following description which proceeds with reference to the following illustrative drawings.

BRIEF DESCRIPTION OF THE DRAWINGS

FIG. 10A-G shows that β-adrenergic pathway stimulation ameliorates lysosomal dysfunction in PS1KO cells. A) Elevated lysosomal pH in PS1KO cells is restored to WT levels by the addition of the β-adrenergic agonists isoproterenol and clenbuterol, but remains unchanged by the addition of the β-adrenergic antagonist alprenolol and the α-adrenergic agonist phenylepherine. Treatment of PS1KO cells also restores CatB activity as determined by MR-CatB staining (B), decreases LC3-II positive puncta (an indicator of autophagic dysfunction) (C), restores turnover of the autophagy substrate P62 (D), and decreases the number and load of autophagic vacuoles in the cells as determined by TEM (E). Pretreatment with the PKA inhibitor H89, or the b-AR antagonist propranol both prevent the action of isoproterenol, demonstrating that b-AR binding and PKA activation are integral parts of the pathway leading to corrected lysosomal pH regulation (F). Moreover, addition of forskolin, an adenylate cylase inhibitor and rolipram, a PDE4 inhibitor both resulted in decreased lysosomal pH in PS1KO cells, further validating that the action of isoproterenol occurs via the canonical β-adrenergic pathway (G).

DETAILED DESCRIPTION

Figure 1:
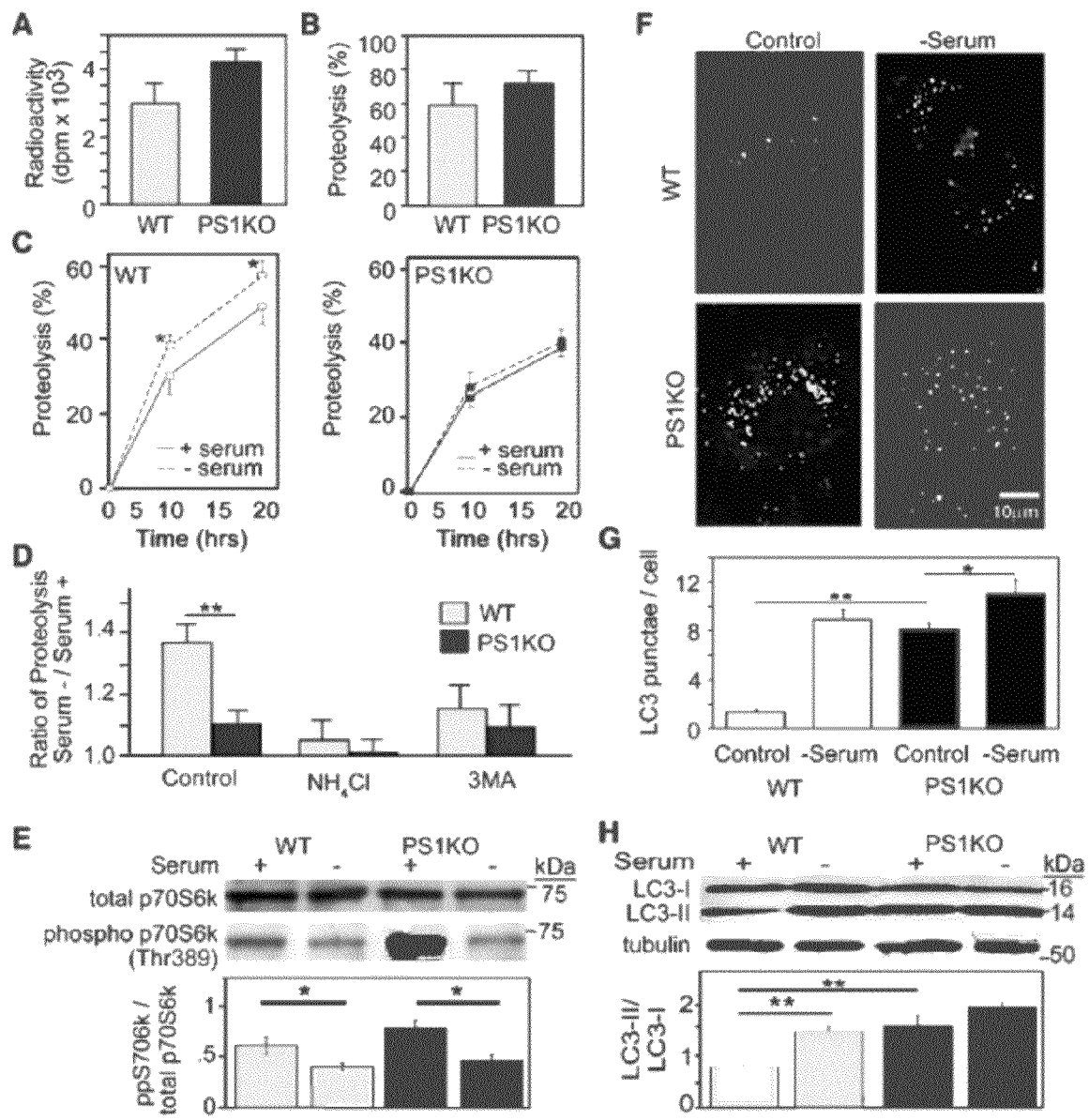
FIG. 1A-H depicts protein turnover in PS1 KO cells: (A) Blastocysts from WT or PS1 KO mice were incubated with [$^3$H]-leucine and the incorporation of radio-labeled leucine to proteins was calculated as a measure of protein synthesis. (B) Following labeling with [$^3$H]-leucine, the proteolysis of short-lived proteins in the same cells was measured after a chase period. (C) Degradation of long-lived proteins was measured in WT (left panel) and PS1 KO cells (right panel). After incorporation of [$^3$H]-leucine, cells were incubated in serum-supplemented or -deprived medium during the chase period (up to 20 hrs) (* for $p<0.05$, $n=9$). (D) The increase in proteolysis at 12 hrs after removal of serum relative to serum-replete conditions was determined for WT and PS1 KO cells that were untreated (control) or were treated with NH$_4$Cl or 3MA (** for $p<0.001$, $n=9$) as a determinant of the autophagic contribution of protein degradation. (E) Western blots of total p70S6K and phospho (Thr389)-p70S6K and their levels quantified by densitometry in WT and PS1 KO cells following growth in the presence or absence of serum for 6 hrs (* for $p<0.05$, $n=3$). (F) LC3 immunostaining of WT and PS1 KO cells following incubation in the presence and absence of serum. Scale bar represents 10 μm. (G) Percentages of cell area occupied by LC3 puncta were analysed using ImageJ software (see Methods) (* for $p<0.05$ and  for $p<0.001$, $n=50$). (H) LC3-II Western blots and graphs depicting results of densitometric analyses of LC3-II and LC3-I immunoreactivity and expression as LC3-II/LC3-I ratios using tubulin as a loading control ( for $p<0.001$, $n=3$). All values are the mean±S.E.M.

Macroautophagy is a lysosomal degradative pathway essential for neuron survival. The present inventors show herein that proteolysis during macroautophagy requires the Alzheimer's disease (AD)—related protein, presenilin-1 (PS1). In PS1-null blastocysts, substrate proteolysis and autophagosome clearance during macroautophagy are prevented due to a selective impairment of autolysosome acidification and cathepsin activation. Neurons in mice hypomorphic for PS1 or conditionally depleted of PS1 display similar abnormalities. These deficits are caused by failed targeting of the v-ATPase V01a subunit to lysosomes. N-glycosylation of the V01a subunit, essential for its efficient ER-to-lysosome delivery, requires the selective binding of PS1 holoprotein, to the unglycosylated subunit and the Sec61α/oligosaccharyltransferase complex. PS1 mutations causing early-onset AD produce a similar lysosomal/autophagy phenotype in fibroblasts from AD patients. PS1 is therefore essential for v-ATPase targeting to lysosomes, lysosome acidification, and proteolysis during autophagy. Disruption of autophagy function by PS1 mutations promotes accumulation of pathogenic proteins and neuronal death in AD. See, for example, FIGS. 1-9.

The results presented herein, therefore, demonstrate that reduced activity of lysosomal proteases is associated with or correlated with disruption of autophagy and promotes accumulation of pathogenic proteins and neuronal death in AD. This stands in marked contrast to prevailing thought in the field that increased or hyperactive lysosomal protease activity was linked to AD. Hook et al. (2010, Biol. Chem. 391:861; the contents of which is incorporated herein by reference in its entirety), for example, proposes that inhibitors of the lysosomal protease cathepsin B represent candidate drugs for AD. Additionally, systemic Z-Phe-Ala-diazomethylketone (PADK) injections in APPSwInd and APPswe/PS1DE9 mice caused 3- to 8-fold increases in cathepsin B protein levels and 3- to 10-fold increases in the enzyme's activity in lysosomal fractions. These findings indicate that pharmacologically-controlled lysosomal modulation reduces Aβ1-42 accumulation, possibly through intracellular truncation that also influences extracellular deposition, and in turn offsets the defects in synaptic composition and cognitive functions. The selective modulation promotes clearance at different levels of Aβ pathology and provides proof-of-principle for small molecule therapeutic development for AD and possibly other protein accumulation disorders (Butler et al., 2011, *PLoS ONE*. 6:e20501; the contents of which is incorporated herein by reference in its entirety).

While the paradigm of elevated cathepsin activity in AD is one to which even the inventors used to subscribe, a number of other studies demonstrate an opposite effect wherein cathepsin activity is reduced in AD. This shift in understanding is based upon studies that include our own (Lee et al, 2010, Cell 141:1146; the contents of which is incorporated herein by reference in its entirety) which is described herein. Moreover, a study by Urbanelli and colleagues demonstrated that CatD expression is decreased in AD fibroblasts. Overall these results reinforce the hypothesis that lysosomal impairment may be involved in AD pathogenesis and can be detected not only in the CNS but also at a peripheral level. (Urbanelli et al., 2008, *Neurobiol Aging*. 29:12-22; the contents of which is incorporated herein by reference in its entirety).

Accordingly, the present inventors have made the surprising discovery that autophagic defects observed in AD are due, at least in part, to impaired lysosomal activity which results from elevated pH levels in lysosomes of cells and that this aberrancy leads in turn to a general reduction in lysosomal protease activity.

Further to the above point, the discovery that AD is associated or correlated with a general reduction in lysosomal protease activity is also surprising. Prior to the present discovery, the prevailing thought pertaining to lysosomal proteases and AD was that particular lysosomal proteases, such as, for example, cathepsin B, were linked to AD. See, for example, Mueller-Steiner et al. (2006, Neuron 51:703); Sun et al. (2008, Neuron 60:247); Cole et al. (2006, Neuron 51:671); and U.S. Pat. No. 7,951,367. The idea that the activity of lysosomal proteases is generally impaired in cells of AD patients and that this generalized malfunction of the lysosome results in autophagic defects in such cells was realized only with the disclosure of the results presented herein.

Many researchers have, however, demonstrated the close relationship between lysosomal dysfunction and morphology in AD. Lysosomal dysfunction may be the earliest histological change in AD (Nixon et al., 2000, *Neurochem Res*. 25:1161-1172). Amyloid plaques are full of active lysosomal hydrolases, implying that plaques may originate from lysosomal rupture. Cathepsins D and E (intracellular aspartyl proteases) influence the generation of Aβ peptides within the endosomal-lysosomal pathway as a result of their ability to exhibit β- and γ-secretase like-activity. Inhibition of cathepsin activity causes a rapid and pronounced build-up of potentially amyloidogenic protein fragments (Bahr et al., 1994, *Exp Neurol*. 129:81-94). On the other hand, the failure to degrade aggregated Aβ1-42 in late endosomes or secondary lysosomes was proposed as a mechanism that contributed to intracellular accumulation of Aβ in AD. Additionally, the cysteine protease cathepsin B in lysosomes degrades Aβ peptides, especially the aggregation-prone species Aβ1-42. Cathepsin B deletion increases Aβ1-42 levels and worsens plaque deposition in mice expressing familial AD mutant human APP (Mueller-Steiner et al., 2006, *Neuron*. 51:703-714; Zhang et al., 2009, *Acta Biochimica et Biophysica Sinica*. 41:437-445). However, in each of these cases the focus of studying lysosomal dysfunction was completed in an effort to elucidate the mechanisms of Aβ toxicity and build up in the cell, with the overall question of generalized lysosomal dysfunction as it pertains to autophagic defects remaining unexplored. It was not until the discovery of the results contained herein that alteration in lysosomal pH was described as a mechanism for these lysosomal defects, including the dysregulation of protease activity, and that in turn, these defects resulted in a delay in autophagic turnover, resulting in a build up of autophagic vesicles and intermediates.

Based on the findings presented herein, the therapeutic effects of elevating lysosomal pH were evaluated. Pursuant to this object, the present inventors have shown that elevated lysosomal pH in PS1 KO cells is restored by the β-adrenergic agonists isoproterenol and clenbuterol to normal levels or even hyperacidic levels, whereas the β-antagonist alprenolol or α-adrenergic agonist phenylepherine did not affect lysosomal pH. The present inventors also demonstrated that isoproterenol (200 μM, 6 h) restored to WT levels the following in PS1KO cells: a) lysosomal pH; b) Cat B activity as measured by MR-Cat B; and reversed c) LC3 puncta accumulation determined by LC3 immunocytochemistry (ICC), d) p62 accumulation, and e) AV accumulation by EM morphometry [total area occupied by AVs per EM field ($\approx$1 cell per field)]. In addition to these promising results pertaining to therapeutic effect for isoproterenol, the present inventors have also demonstrated that clenbuterol is an excellent candidate β-agonist compound for the treatment of AD because it has the desired consequences on lysosomal pH and autophagy in PS1-deleted cells at clinically relevant concentrations, has a good safety profile, and has been used in humans for other indications. See, for example, FIGS. 10-11.

The present findings, which are supportive of the potential for isoproterenol and derivatives thereof for treating patients with AD, are surprising in light of the results and conclusions of Sun et al. (2005, FEBS Letters 579:251). More particularly, Sun et al. disclose that bilateral injection of isoproterenol into the hippocampus induces Alzheimer-like hyperphosphorylation of tau and spatial memory defects in rats. In marked contrast, results presented herein indicate a positive clinical outcome upon administration of isoproterenol to AD patients.

Building on the findings outlined herein, clenbuterol and other β-adrenergic agonists in the cAMP/PKA pathway have been tested, including, for example, forskolin (an adenylyl cyclase activator) and rolipram (a specific inhibitor of PDE4), both of which can be used as positive controls in experiments going forward. As shown, for example, in FIG. 11, the effects of multiple classes of compounds on restoring lysosomal pH in PS1KO blastocysts have been investigated. As shown therein, PS1KO cells were treated with a variety of compounds, including β-adrenergic agonists (Clen, Xam), cAMP elevating compounds (For, Rol), and Ca2+ pump inhibitors (Nic), at the indicated concentrations, followed by measurement of lysosomal pH. One way ANOVA analysis was performed with a Dunnet's Multiple Comparison Post-test to assess the significance in difference relative to WT pH. Clenbuterol, forskolin, and rolipram treatment resulted in a lysosomal pH that did not differ significantly from that of WT lysosomal pH. As a consequence, these agents are categorized as effective for decreasing lysosomal pH to a level similar to that of WT cells. Abbreviations used are as follows, Clen=clenbuterol; For =forskolin; Rol=Rolipram; Nic=Nicardipine; Xam=xamoterol; Res=resveratrol; Cur=curcumin; Ril=Rilmenidine.

In all such experiments, those already performed and in screening assays and method, cAMP levels can be monitored by ELISA (Abcam). PKA activation can be assessed using a non-toxic dose of H-89 [Chijiwa et al. J Biol Chem, 1990. 265(9): 5267-72; the content of which is incorporated herein by reference in its entirety] (as determined by MTS assay) and confirmed via western blotting (WB) against both phosphorylated (active) and whole PKA protein. PI3K activation can be assessed using LY294002 [Vlahos et al. J Biol Chem, 1994. 269(7): 5241-8; the content of which is incorporated herein by reference in its entirety] and inhibition of AKT phosphorylation by WB. To implicate non-proton ionic species in the mechanism of lysosomal pH rescue, cells can be pretreated with the ionophore valinomycin to block active ion transport across lysosomes. This eliminates lysosomal pH restoration by clenbuterol, if it is occurring by altering ion transporter regulation. The possible involvement of TRPML1, a lysosomal $Ca^{2+}$ channel [Xu et al. Proc Natl Acad Sci USA, 2007. 104(46): 18321-6; the content of which is incorporated herein by reference in its entirety] in the mechanism can be tested by pre-treating with verapamil prior to β-adrenergic agonist addition. Should TRPML1 be implicated in this pathway, $Ca^{2+}$ levels can be monitored using commercial fluorogenic substrates, which include dextran conjugated Fura-2 among others, allowing $Ca^{2+}$ levels to be analyzed in the lysosome. Should CLC-7, and by extension, be important, the level of lysosomal Cl$^-$ can be assayed directly by monitoring the endocytic uptake and fluorescent intensity of the Cl$^-$ indicator SPQ (Invitrogen) as per Verkman [Verkman et al. Am J Physiol, 1990. 259(3 Pt 1): C375-88; the content of which is incorporated herein by reference in its entirety]. TRPML1 and CLC-7 protein levels are measured by Western blot with anti-TRPML1 and anti-CLC7 antibodies (Abcam). Since no specific inhibitors of CLC-7 exist, CLC-7 siRNA can be used to knock down prior to drug treatment with clenbuterol and the in situ assays described above, an experiment that can also be performed on TRPML1. The influence of additional ionic transport in pH regulation of the lysosome can also be investigated, since both Na+ and K+ flux have been demonstrated in the lysosome, although the exact transporters and exact role in pH regulation remain unclear [Moriyama. Biochem Biophys Res Commun, 1988. 156(1): p. 211-6; Orlowski et al. Curr Opin Cell Biol, 2007. 19(4): 483-92; the contents of each of which is incorporated herein by reference in its entirety]. Therefore, utilization of a generic K+ channel inhibitor or a Na+ channel inhibitor may provide useful data in determining what is occurring at the lysosome after β-adrenergic treatment. Although unlikely based on our preliminary data, restoration of vATPase activity as a contribution to rescue will be tested using techniques in Lee et al. [Cell, 2010. 141: 1146-58; the content of which is incorporated herein by reference in its entirety] to measure possible restoration of vATPase levels.

The cell signaling pathway(s) responsible for these therapeutic effects in PS1-deleted and control cells can, moreover, be tested using appropriate pharmacologic inhibitors and/or siRNA constructs. Lysosomal pH is maintained via the coordinated action of the vATPase and chloride, sodium, calcium, and potassium transporters [Forgac et al. J Biol Chem, 1999. 274(19): 12951-4; Graham et al. J Exp Biol, 2000. 203(Pt 1): 61-70; the contents of each of which is incorporated herein by reference in its entirety]. Activation of β-adrenergic signaling results in the downstream stimulation of protein kinase A (PKA) which interestingly has been shown to regulate the activity of TRPML-1 or Mucolipin 1, an inwardly rectifying lysosomal cation/proton channel, as well as the Cystic Fibrosis Transporter, a known chloride transporter [Vergarajauregui et al. Biochem J, 2008. 410(2): 417-25; Tabcharani et al. Nature, 1991. 352(6336): 628-31; Berger et al. The Journal of Clin Inv, 1991. 88(4): 1422-31; the contents of each of which is incorporated herein by reference in its entirety]. Recent studies have directly suggested a role for TRPML1 in regulation of lysosomal pH. Moreover, transporters in general have been implicated in lysosomal pH regulation [Steinberg et al. J Cell Biol, 2010. 189(7): 1171-86; the content of which is incorporated herein by reference in its entirety]. CLC-7, a chloride/proton antiporter, may be relevant to the production of the counter-ion flux necessary to maintain lysosomal pH [Graves et al. Nature, 2008. 453(7196): 788-792; the content of which is incorporated herein by reference in its entirety]. Additional studies to investigate lysosomal transporters that regulate pH will provide insight into a mechanistic analysis of the transporter(s) modulated by adrenergic agonists. The application of this approach is, furthermore, not limited to PS-related AD but increasing acidification could be a general approach to enhancing lysosomal efficiency as previously shown using ascorbate to enhance autophagy in vitro [Martin et al. J Neurochem, 2002. 82(3): 538-49; the content of which is incorporated herein by reference in its entirety].

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

Thus, in a broad aspect, the present invention extends to the treatment of AD in mammals, particularly in humans, using agents or compounds that enhance lysosomal activity. In a particular aspect, methods are provided for treating AD, comprising administration of one or more agents or compounds that enhance lysosomal activity. The use of one or more agents or compounds that enhance lysosomal activity for treating is also encompassed herein. Such agents and compounds restore impaired lysosomal activity, as determined by measuring elevated pH levels in lysosomes, by lowering the pH level to normal pH levels or even hyperacidified levels. An elevated pH level in lysosomes is equal to or greater than about 5.2. Impaired lysosomal activity can also be determined by detecting reduced levels of lysosomal protease activity in cells of the subject. The reduced levels of lysosomal protease activity reflect a general or overall reduced activity level of essentially all or nearly all of the lysosomal proteases. The reduced levels of lysosomal protease activity observed in the cells of the subject are, therefore, not due to reduced levels of activity for a specific lysosomal protease. Reduced levels of lysosomal protease activity in cells of the subject is associated with reduced activity of at least three lysosomal proteases.

Exemplary compounds for the methods and uses described herein include agents or compounds that enhance lysosomal activity, including: β-adrenergic agonists, cAMP agonists, Ca2+ pump inhibitors, phosphodiesterase inhibitors, chloride channel activators, L-type calcium channel blockers, purinergic agents, anti-oxidants, cAMP-activated protein kinase inhibitors, cathepsin activators, sirtuin activators, lipofuscinolytics, ceroid depletors, imidazole-1 receptor agonists, calpain inhibitors, and anti-lipolytic agents. Particularly exemplary agents include: β-adrenergic agonists, cAMP agonists, Ca2+ pump inhibitors, and phosphodiesterase inhibitors. Exemplary β-adrenergic agonists include: isoproterenol or a derivative thereof and clenbuterol or a derivative thereof.

Specific compounds from each of the categories listed above are generally available commercially from a number of suppliers. The bulk of the compounds used, or to be used in the screens described herein, are obtainable directly from Sigma-Aldrich Inc, a global leader in chemical and biochemical synthesis and distribution. For example, the beta-adrenergic compounds Isoproterenol (Cat#16504) and Clenbuterol (Cat# C5423) were obtained from this supplier. Following is a list of sample compounds encompassing the categories above and their catalog numbers as indicated by Sigma-Aldrich: Forskolin (F6886), Rolipram (R6520), Dorsomorphin dihydrocholoride (P5499), Genistein (G6649), Lithium Carbonate (L4283), Vitamin E (tocopherol) (T3251), Lipoic acid (07039), Curcumin (C1386), Acetylhomocysteine thiolactone (A16602), Acetylcarnitine (A1509), Pimozide (P1793), Nicardipine (N7510), Loperamide (L4762), Rilmenidine (R134), and Salmeterol (S5068).

Derivatives of any of the above listed agents, including isoproterenol and clenbuterol, which enhance lysosomal activity are suitable for use in the invention. The action of such derivatives can be determined by the skilled artisan by recognized methods or those disclosed herein.

One skilled in the art can readily determine or assess the suitability of other compounds for use in the invention, including by screening in the cellular assays described herein, or in animal models of AD disease such as those described herein, or by determining the ability of a potential compound to enhance lysosomal activity by decreasing lysosomal pH and increasing lysosomal protease activity in isolated lysosomal preparations.

The term "impaired lysosomal activity" as used herein refers to a condition in which degradation of lysosomal contents is significantly delayed or completely abolished.

The term "elevated lysosomal pH" as used herein refers to increased alkalinity of the lumenal lysosomal pH. More particularly the term refers to a pH that is equal to or greater than about 5.2.

The term "reduced levels of lysosomal protease activity" as used herein refers to a significant decrease in the rate at which a given lysosomal protease degrades its specific substrates, or an overall decrease in the rate of degradation of lysosomal substrates, encompassing all resident lysosomal proteases. The term may also be used to describe lysosomes or cells comprising same that have reduced activity of at least three lysosomal proteases. The term also applies to subjects afflicted with disorders such as AD, wherein the subject's cells display reduced levels of lysosomal protease activity.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term "prophylaxis" is related to "prevention", and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

As described herein, samples may be isolated from subjects before, concurrently, and/or after treatment with or use of an agent for enhancing lysosomal activity. Such samples may comprise or consist of skin fibroblasts, lymphocytes or other white cell subtypes, particularly with respect to assays pertaining to lysosomal pH or other lysosomal functions. For assays of cathepsin D (catD) specific activity, samples comprising blood plasma or serum, urine, saliva, or cell samples such as, for example, skin fibroblasts, lymphocytes or other white cell subtypes, could be assayed for catD alterations. In a particular embodiment, the sample is cerebrospinal fluid isolated from the subject. In a more particular embodiment, the cerebrospinal fluid is lumbar cerebrospinal fluid.

Samples may be isolated from subjects/patients and assayed for purposes relating to diagnosis of the subject/patient and/or subject/patient stratification, particularly with respect to evaluation of the subject with respect to anticipated responsiveness to an agent or compound described herein, or assessment of efficacy of an agent or compound described herein after treatment with or use thereof has been initiated.

The agents and compounds and derivatives thereof of use in the invention may be prepared in pharmaceutical compositions, with a suitable carrier and at a strength effective for administration by various means to a patient experiencing an adverse medical condition associated with AD for the treatment thereof. A variety of administrative techniques may be utilized, among them parenteral techniques such as subcutaneous, intravenous and intraperitoneal injections, catheterization and the like. Average quantities of the agents and compounds and derivatives thereof may vary and in particular should be based upon the recommendations and prescription of a qualified physician or veterinarian.

The present invention further contemplates therapeutic compositions useful in practicing the therapeutic methods of this invention. A subject therapeutic composition includes, in admixture, a pharmaceutically acceptable excipient (carrier) and one or more of an agent, compound or derivative thereof, as described herein as an active ingredient.

The preparation of therapeutic compositions which contain agents, compounds, or derivatives thereof as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An agent, compound, or derivative thereof can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic agent, compound, or derivative thereof-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and subsequent shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

Analysis of Lumbar Cerebrospinal Fluid (CSF)

Figure 12:
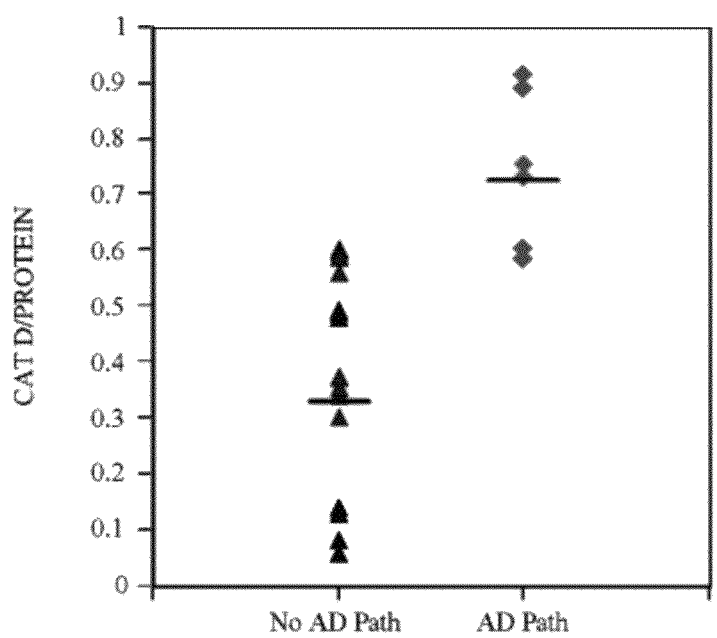
FIG. 12 depicts a graph showing that elevated levels of Cat D are detected in lumbar CSF isolated from patients with mild to severe Alzheimer's disease: Cat D levels in 6 subjects with AD pathology and 12 non-Alzheimer controls (Group 2) were determined by the standardized ELISA procedure as described herein below and expressed as a ratio of Cat D (ng/ml CSF) to total protein (μg/ml). Each data point represents the ratio for a single individual. The horizontal bars indicate the mean value for each group.

The present inventors have, moreover, determined that increased levels of the lysosomal protease cathepsin D (cat D) in lumbar CSF serves as a surrogate marker for AD. See FIG. 12. As shown therein, the cathepsin D levels are convincingly elevated by measuring the protein level in AD patients relative to subjects with no apparent AD pathology. Accordingly, analysis of lumbar CSF provides a viable alternative to ventricular CSF analysis and confirms that cat D levels are increased substantially in both ventricular and lumbar CSF in AD patients relative to controls. The present findings, therefore, confirm and extend those of Schwagerl et al. (1995, J. Neurochem. 64:443-446; the entire content of which is incorporated herein by reference in its entirety), which demonstrated elevated levels of cat D in ventricular CSF isolated from AD patients relative to that of other late-onset neurodegenerative diseases. Schwagerl et al., moreover, showed that the abnormally accumulated cat D included a high proportion of inactive cat D enzyme. In keeping with the results presented herein, elevation of inactive/less active catD also serves as a likely surrogate marker of AD as well. Thus, either of elevated total catD or inactive/less active catD in AD patients may be used as a surrogate marker for AD and, furthermore, indicate if an AD patient that would benefit from the methods described herein. A definitive diagnosis of AD, would also include an analysis of other tau and amyloid markers of AD, so as to distinguish AD from other conditions.

General Methods

Purification of Human Brain Cat D and Enzyme Assay:

Cat D from postmortem human brain is purified as described (Nixon, 1995, Neurchem. Int. 27:385). Briefly human brain cytosolic fraction is precipitated by acid followed by ion exchange chromatography and affinity chromatography on pepstatinyl-aminohexyl sepharose 6B (Nixon, 1995, supra). Its purity is assessed by chemical, enzymatic as well as immunological properties. Cat D activity can be measured by a modification of the method of Anson (1940) using [$^{14}$C] methemoglobin as substrate prepared by the method of Dottavio-Martin and Ravel (1978, Anal Biochem 87, 562-565). A 50 µl aliquot of enzyme is incubated at 37° C. with 100 µl of 0.4M acetate buffer pH 3.2, containing 10 mg/ml [$^{14}$C] methemoglobin (20,000 cpm). Cat D activity is expressed in terms of methemoglobin degrading activity, as cpm present in TCA soluble fraction. One unit of enzyme activity is defined as the ability to degrade one nanomole of methemoglobin per minute.

Preparation and Biotinylation of Monoclonal Antibodies to Cat D:

Three hybridoma cell lines, namely CD1, CD3.1 and CD5.1 can be thawed and large quantities of antibodies prepared either by growing hybridoma in roller bottles or by generating ascites fluid (see *Antibodies—A Laboratory Manual*, Harlow and Lane, eds., Cold Spring Harbor Laboratory, New York (1988), which is incorporated herein by reference). Pure IgG fractions are purified from the media and/or ascites fluid as follows: Samples are concentrated by ammonium sulfate precipitation followed by dialysis. The dialysate is loaded on Protein A sepharose column and bound IgG is eluted by 0.1 M glycine HCl buffer pH 2.5. The acid eluate is neutralized by 1 M Tris, pH 11.0 followed by dialysis against PBS pH 7.4. The purified IgG fractions are examined by ELISA and Western blotting before biotinylation. Biotinylation is carried out using a kit supplied by Molecular Probes (Eugene, Oreg.), according to the procedure suggested by the manufacturer. Antibody solution (10 mg/0.75 ml) in 0.1 M bicarbonate buffer (prepared by adding sufficient 1M sodium bicarbonate pH 9.0) is mixed with 100 µl freshly dissolved biotin-N-hydroxy succinimidyl ester (10 mg/ml in DMSO) at room temperature for 1 hour. The reaction is stopped by adding 150 µl 1 M sodium glutamate solution and is incubated again for 1 more hour followed by dialysis against TBS overnight with several changes. CDI monoclonal is blotting later and used for ELISA as described. One skilled in the art would, however, appreciate that the above protocol is not limited to the antibodies listed herein above but can be performed using any monoclonal or polyclonal antibody specific for Cat D ELISA Procedure:

Cat D can be examined by a sandwich ELISA in which the antigen including standard Cat D and unknown is bind to Cat D antibody coated onto microwells and bound antigen can be detected by biotinylated anti-Cat D antibody.

Cat D ELISA Protocol:

CSF sample preparation: Immediately after collection CSF samples are centrifuged at 15000 g to remove any possible cellular debris and stored at −70° C. in multiple smaller aliquots to avoid freezing and thawing. Suitably diluted lumbar CSF and varying concentrations of purified Cat D (0-5 ng) is tested in a total volume of 100 µl in 10 mM Tris/HCl; 10 mM NaCl; 10 mNaN$_3$, pH 8.5 at 37° C. overnight onto Cat D antibody coated Nunc-Immuno microtiter plates (high binding with low background, Nunc Apogent, Rochester, N.Y.). Each sample/standard is tested in duplicate. Four wells will contain no standard Cat D, two for measuring the background absorbance and two for use as substrate blanks. The plates will then be covered with plastic wrap and incubated at 37° C. overnight. They are then washed with TBS containing 0.05% Tween 20 (Wash buffer, TBS-Tris buffered saline, 50 mM Tris/HCl, pH 7.4; 150 mM NaCl) and blocked with 100 µl of 0.1% casein; 0.05% Tween 20 in TBS (blocking buffer), sealed and incubated for 1 hr at 37° C. After blocking, the buffer is removed and the plates are washed 5× with 300 µl of wash buffer. 100 µl of diluted HRP coupled anti-Cat D antibody (CD 5.1, 100 ng) in blocking buffer is added to all microwells except the substrate blank well and incubated at 37° C. for 3 hours followed by washing again (4×300 µl) using plate wash buffer. A calibration curve can be constructed relating the RLU to the concentration of Cat D to enable quantities of Cat D in CSF to be determined. Samples at 3 concentrations can be tested in 3-6 separate assays to determine interassay variation. Samples mixed with 2-3 concentrations of standard Cat D can be tested to determine intra-assay variation and recovery.

Detailed Methods Pertaining to Examples and Assays

Cell Lines and Mouse

Murine blastocysts with different presenilin (PS1) genotypes (WT, BD6; PS1 KO BD15; PS1/2 KO, BD8) previously characterized by Lai et. al. (2003, J Biol Chem 278, 22475-22481), were used in this study. In addition, human PS1 wt was stably transfected into the BD8 line (Laudon et al., 2004). The cells were grown in 35 mm dishes in DMEM supplemented with penicillin/streptomycin (Invitrogen), 15% fetal bovine serum (Hyclone), and β-mercaptoethanol (Sigma). Human fibroblasts lines, acquired from the Coriell Institute (Camden N.J.), Karolinska Institute (Upsala, Sweden), University di Firenze (Italy) and University of Western Australia (Perth), were maintained in MEM (Invitrogen, Carlsbad Calif.) with 15% FBS (Hyclone, Logan, Utah) at 37° C. and 5% $CO_2$. PS1 hypomorph (Rozmahel et al., 2002) and PS cKO mice (Saura et al., 2004) were studied at 13 month and 2-3 month, respectively, together with age-matched controls. All animal experiments were performed according to "Principles of Animal Care" (NIH, 1985) and approved by the Institutional Animal Care and Use Committee at the NM.

Antibodies and Reagents

Rabbit pAb to LC3 (1/500) (Koike et al., 2005 (2005) Am J Pathol 167, 1713-1728.) and LC3 (1/200, Novus) were used for cell and mouse brain, respectively, immunofluorescence studies and a polyclonal LC3 (generated in house, 1/1000) (Yu et al., 2005) was used for immunoblotting, anti-murine LAMP (LAMP-2: ABL-93, 1/200 and LAMP-1: 1D4B, 1/5 or H4A3, 1/200) mAb was purchased from Developmental Studies Hybridoma Bank. Rabbit anti-Cathepsin D pAb (1/1000) was purchased from Scripps Laboratories for MeOH fixed cell ICC, Rabbit anti-Cathepsin D pAb (1/5000) was generated in house for 4% PFA fixed ICC and western blot, and rabbit polyclonal antibody to Cat D (1:50, IEM) was purchased from DAKO. The Anti-PDI mouse mAb (1/5000) and Anti-GRP94 rat mAb (9G10, 1/10000) were purchased from Assay designs. Anti-Calnexin mouse mAb (1/1000) was from Affinity Bioreagent. The mouse monoclonal anti-LBPA antibody (1/2) was a generous gift from Dr. Jean Gruenberg. Anti-EEA1 mouse mAb (clone 14, 1/1000) was purchased from BD Bioscience. The mouse monoclonal anti-CI-MPR (clone 2G11, 1/500) and mouse monoclonal anti-rab7 were from Abcam. Guinea pig polyclonal anti-p62 (GP62-C, 1/2000) was from Progen Biotechni and mouse monoclonal anti-human p62 (1/1000) was from BD transduction. LysoTracker Red DND-99 (1/10000), LysoSensor yellow/blue-Dextran, Bodipy-FL-Pepstain A (1 Kg/ml), DAMP (30 µM stock), and mouse monoclonal antibody to DNP (1:50) were from Invitrogen. Total p70S6K (#9292, 1/1000) and phospho-p70S6K (#9206, 1/1000) were purchased from Cell Signaling. Anti-PS1 rabbit pAb (Ab14) was a generous gift from Dr. Sam Gandy, anti-PS1-NTF rabbit pAb (34-4600, 1/1000) was purchased from Zymed. Anti-PS1 loop mouse mAb (MAB5232, 1/1000) and anti-nicastrin mouse mAb (MAB5556, 1/1000) were purchased from Chemicon. β-tubulin (clone 2-28-33, 1/5000), anti-actin (clone AC-40, 1/5000), and rabbit polyclonal anti-GAPDH (1/5000) were purchased from Sigma. A rabbit pAb against mouse v-ATPase V0a1 (W249, 1/5000) and mouse pAb against human v-ATPase V0a1 (Osw2, 1/500) were generous gift from Dr. Satoshi Sato and other rabbit pAb against V0a1 subunit of the vacuolar proton pump (1/500) was purchased from Synaptic Systems. The v-ATPase V1 B antibody (H-180, 1/200) was purchased from Santa Cruz Biocech. Following reagents were used for autophagy modulation experiments. Rapamycin (Rapa, final 10 nM), ammonium chloride ($NH_4Cl$, final 20 mM), bafilomycin A1 (final 0.2 µM) and 3-methyladenine (3MA, final 10 mM) were from Sigma and leupeptin (final 0.3 mM) was from Peptide Institute Inc. The γ-secretase inhibitor (L685,458) was purchased from Sigma.

Gel Electrophoresis, Immunoblotting and Deglycosylation

Immunoblotting was performed as previously described (Yu et al., 2005). Briefly, cells used for Western blot analysis were lysed in buffer containing 50 mM Tris (pH=7.4), 150 mM NaCl, 1 mM EDTA, 1 mM EGTA, 1% Triton X-100 and 0.5% Tween-20 with protease and phosphatase inhibitors. Following electrophoresis on 4-20% gradient gel (Invitrogen), proteins were transferred onto 0.45 µm PVDF membranes (Millipore) and the membrane was incubated overnight in primary antibody then incubated with HRP conjugated secondary antibody. The blot was developed by ECL-kit (GE Healthcare). To assess v-ATPase V0a subunit glycosylation, lysate from WT and PS1KO cells were either treated for 24 hrs at 37° C. with PNGase F or O-glycanase using an enzymatic deglycosylation kit according to the manufacturer's instructions (PROzyme) or with Endo H (New England Biolabs) for 24 hrs at 37° C. Total glycoproteins were isolated using Glycoprotein Isolation Kit, ConA according to the manufacturer's instructions (Thermo Scientific).

Subcellular Fractionation

Homogenate (0.5 ml) was layered on the top layer of 10, 15, 20, 25, and 30% Optiprep (Sigma) step gradient, 2.3 ml each, into polyallomer tubes (Beckman) and centrifuged in a SW-40Ti rotor with a model L8-80M Beckman ultracentrifuge (100,000 g, 16 hours, 4° C.). After centrifugation, the gradients were fractionated into 0.5 ml fractions. 40 µA of each collected fraction was mixed with an equal volume of sample buffer and then loaded onto gels. The homogenates were fractionated into cytosolic and membrane fractions by high speed centrifugation (150,000×g, 60 min) and equal protein was loaded on gel following 55° C. for 10 min incubation with 2× urea sample buffer. All data represent an average at least three independent experiments.

Autophagic Vacuole Isolation

AVs were isolated by centrifugation in a discontinuous metrizamide density gradient (Marzella et al., 1982) for each cell line. Cells ($5\times10^8$) were serum-deprived overnight to induce autophagic activity prior to AV isolation. The cells were collected, disrupted by nitrogen cavitation then homogenized in 3 volume of 0.25 M sucrose in a glass homogenizer with Teflon pestle for 10 strokes. The homogenate was filtered through double gauze and then spun at 2000×g for 5 min to yield a supernatant and pellet of unbroken cells and nuclei. The supernatant was centrifuged at 17,000×g for 12 min to yield a pellet and a supernatant which was spun again at 100,000×g for 1 hr to yield a pellet containing ER and a supernatant containing cytosol. The pellet from the 17,000×g centrifugation was resuspended in the same volume of 0.25 M sucrose and spun again at 17,000×g for 12 min. The pellet was resuspended in 1.9 ml of 0.25 M sucrose and 2.8 ml of metrizamide (Mtz). This mixture (2.4 ml volume) was loaded on top of a 26% (4 ml), 24% (2 ml), 20% (2 ml) and 15% (2 ml) Mtz step gradient matrix. The sample on the Mtz gradient was centrifuged at 247,000 rpm for 3 hrs in an ultracentrifuge using an SW41 rotor. Each gradient interface was collected and diluted in 0.25 M sucrose. The samples were then pelleted at 24,000×g for 10 min. Light AVs (AV10) were present in the 15-20% fraction, while heavy AV (AV20) was present in the 20-24%, lysosomes were in the 24-26% interface, and mitochondria were located in the 26% Mtz area. Fractions were pelleted and immersed in a cacodylate fixation buffer for EM analysis or analyzed directly by Western blot or enzyme assay. All data represent an average at least three independent experiments, unless otherwise indicated.

Ultrastructural and Morphometric Analyses

Following treatments, cells were prepared for EM as previously described and AVs, identified using previous morphological criteria (Yu et al., 2005), were classified and counted on electron micrographs (7900× print magnification) of 20 EM images from different lines in each experimental group.

Lysosomal pH Measurement

For results presented in Example 1, quantification of lysosomal pH was determined using Dextran conjugated Lysosensor Yellow/Blue DND-160 (Invitrogen) as follows. Wild Type and PS1KO blastocysts were grown in High Glucose DMEM+15% FBS with antibiotics to ~90% confluency. Cells were then trypsinized, harvested ($1\times10^6$ cells/ml) and loaded with 1 mg/ml of Lysosensor-dextran for 1 hour at 37° C. with 5% $CO_2$. The cells were then washed 3× in HBSS and aliquoted at 100 µA into a black 96-well microplate. pH calibration was performed according to the protocol established by Diwu et al (Diwu et al., (1999). Chem Biol 6, 411-418). Briefly, wild type and PS1KO blastocysts were treated with 10 µM monensin and 10 uM nigericin in MES buffer (5 mM NaCl, 115 mM KCL, 1.3 mM MgSO4, 25 mM MES), with the pH adjusted to a range from 3.5-7.0. The samples were read in a Wallac Victor 2 fluorimeter (Perkin Elmer) with excitation at 355 nm. The ratio of emission 440/535 nm was then calculated for each sample. The pH values were determined from the linear standard curve generated via the pH calibration samples.

In Vivo Vesicle Acidification Study

The mouse was anaesthetized with a 1% body weight IP injection of chloral hydrate, (400 mg/kg at a concentration of 50 mg/ml, 26 g needle, and volume less than 200 ul) and allowed sufficient time to go down. Under sterile conditions, the subject was then shaved, and cleaned at the site of the surgery, in this case the scalp. The subject was placed in position in a stereotaxic holder with drill (BenchMark). The position of the drill/burr arm was located in right ventricle (−0.22 mm from bregma; L, −1 mm; D/V, −2.5 mm), the coordinates relative to the bregma, were determined by using *The Mouse Brain* (Keith B. J. Franklin and George Paxinos, Academic Press).

Mouse was injected with DAMP (20 µl of 30 mM stock solution prepared in PBS) by intra-ventricular method with 1.5 µl/min speed. After 4 hrs, animals were anesthetized and perfused with a fixative containing 0.1% glutaraldehyde and 4% paraformaldehyde in sodium cacodylate buffer (Electron Microscopy Sciences). Brains were dissected and immersed in the same fixative for 4 hrs and then 40 sagital sections were made using a vibratome. The sections were processed routinely for electron microscopy and embedded in LR white. Ultrathin sections were mounted on nickel grids. Sections were treated with 4% NRS for 2 hrs at room temperature. For DAMP, the sections were incubated with an antibody to DNP (Invitrogen 1:50) and CatD (1:50, DAKO) overnight. Grids were subsequently washed with PBS and incubated for 2 hrs in room temperature with secondary antibody coupled with 10 nm gold. Sections were washed with PBS and were stained briefly with uranyl acetate and lead citrate. Sections were examined and photographed with a Philips CM10 electron microscope.

Intracellular Protein Degradation Measurements

Total protein degradation in cultured cells was measured by pulse-chase experiments (Auteri et al., 1983, J Cell Physiol 115, 167-174). Confluent cells were labeled with [$^3$H]-leucine (2 µCi/ml) for 48 hrs at 37° C. in order to preferentially label long-lived proteins. Following labeling, cells were extensively washed and maintained in complete medium (DMEM+10% fetal bovine serum), under which conditions autophagy is suppressed, or in serum-deprived medium, where autophagy is induced. Under both conditions, after washing the cells, the medium was supplemented with unlabeled 2.8 mM leucine to prevent [$^3$H]-leucine reincorporation into newly synthesized proteins. Aliquots of the medium taken at different time-points were precipitated with 10% TCA, filtered using a 0.22 µm pore membrane and radioactivity in the flow-through was measured. Proteolysis is expressed as the percentage of the initial acid-precipitable radioactivity (protein) transformed to acid-soluble radioactivity (amino acids and small peptides) over time. To inhibit autophagy in this system, 20 mM $NH_4Cl$ or 10 mM 3MA was added immediately after the labeling period and maintained at that concentration throughout the chase. $NH_4Cl$ blocks lysosomal degradation, so this procedure permits one to estimate the relative contributions of lysosomal and non-lysosomal pathways to overall protein degradation. 3MA blocks formation and fusion of autophagosomes to lysosomes and is used to block macroautophagic contributions to proteolysis. Degradation rates of short-half life proteins were determined by the same procedure but after a labeling period of 30 min at 37° C. Nearly all turnover of short-lived proteins is due to proteasomal activity. Protein synthesis was determined as the incorporation of [$^3$H]leucine into acid-insoluble material in the presence of an excess (2.8 mM) unlabeled leucine in the medium. Under these conditions incorporation of radioactivity into protein accurately reflects rates of protein synthesis and minimizes differences due to alteration of amino acid transport and/or intracellular amino acid pool sizes.

Confocal Laser Scanning Microscopy

Immunocytochemistry was performed as previously described (Yu et al., 2005). Secondary antibodies used were from Invitrogen: goat anti-mouse/rabbit/rat Alexa Fluor 488 and goat anti-mouse/rabbit/rat Alexa Fluor 568. Cells were imaged using a plan-Apochromat 40× or 100×/1.4 oil DIC objective lens on the laser scanning confocal microscope, LSM 510 META, with LSM software v3.5 (Carl Zeiss Micro-Imaging Inc). Images were analysed using ImageJ program (NIH). Organelles with low internal pH were labeled by LysoTracker DND-99 dye (Invitrogen) at the final 100 nM for 30 min. Following 4% PFA fixation, cells were further counter stained with Cat D, LMAP1, or LC3 antibody for 4 hrs then visualized with Alexa Fluor 488 conjugated secondary antibody. Active Cat D was labeled by adding Bodipy-FL-pepstatin A directly to the medium at a final concentration of 1 µg/ml for 1 hr. Following 4% PFA fixation, cells were counter stained with Cat D antibody for 4 hrs and visualized with Alexa Fluor 568 conjugated secondary antibody. For assessing Cat B activation, MagicRed-Cathepsin B (Immunochemistry Technologies) for active Cat B was added to the cells at the concentration suggested by company (1:260). Cells were incubated for 30 min with MR-Cathepsin B prior to mounting them under the confocal microscope. To block v-ATPase proton pump activity, ammonium chloride (NH$_4$Cl) was added directly to the medium at a final concentration of 20 mM for 6 hrs prior to LysoTracker addition.

Co-Immunoprecipitation

Wild type mouse blastocysts cells were lysed with lysis butter (50 mM Tris-Cl, pH 8.0, 150 mM NaCl, 100 mM EDTA, and protease inhibitor cocktail) with 1% digitonin. Immunoprecipitations of complex proteins with anti-PS1 pAb, anti-V-ATPase V0a1 subunit pAb, anti-Sec61α, or anti-STT3B were performed using the Seize Primary immunoprecipitation kit (Pierce Biotechnology) (Hiesinger et al., 2005).

Degradation of HRP Internalized by Fluid Phase Endocytosis.

HRP degradation was evaluated in cells that were incubated for 30 min at 37° C. with medium containing 5 mg/ml horseradish peroxidase (HRP) (HRP type II; Sigma) and washed three times with phosphate-buffered saline then chased 37° C. for 1, 2, and 6 hrs with fresh media. Following fixation, the cells were immunolabeled with rodamine-conjugated anti-HRP antibody (Jackson lab).

Enzymatic Assays

Cathepsin B and L activity were assayed as described previously (Nakanishi et al., 1994, Experimental Neurology 126, 119-128) and Cathepsin D activity was assayed using [$^{14}$C]methemoglobin as previously described (Dottavio-Martin and Ravel, 1978). A 50 µl aliquot of enzyme was incubated at 37° C. with 100 µl of 0.4 M acetate buffer (pH 3.2) containing 10 mg/ml [$^{14}$C]methemoglobin. Cathepsin D activity was expressed in terms of methemoglobin degrading activity; one unit of enzyme activity is defined as the capacity to degrade one nanomol of methemoglobin per minute.

Cathepsin D Metabolic Labeling

Cells were grown in a 3.5 cm dish to 5×10$^5$ cells/dish, after which they were metabolically labeled for 30 minutes with 100 mCi/ml [35S]methionine/cysteine (EXPRE35S35S Protein Labeling Mix, NEG0702 14MC: Perkin Elmer) and chased with normal medium for specific periods. The labeled cells were lysed and subsequently processed for immunoprecipitation with anti-rat cathepsin D antibody and protein G-agarose bead (Santa Cruz Biocech). The immunoprecipitates were analyzed by 10% SDS-PAGE.

Transfection of Plasmid

Fibroblast were transfected with mRFP-GFP-LC3 (Kimura et al., 2007, *Autophagy* 3, 452-460) from Dr. Tamotsu Yoshimori (Osaka University) using Lipofectamine 2000 (Invitrogen) according to the manufacturer's instruction. Following transfection, fibroblasts were incubated for 24 hrs and before imaging incubated for another 6 hrs with serum or without serum medium.

Agents and Compounds

A range of concentrations of the compounds listed below, above and below a clinically relevant concentration, can be tested in each case.

Compounds Potentially Capable of Acidifying Compromised Lysosomes:

β-adrenergic receptor agonists—e.g., isoproterenol (Liu et al., *Invest Opthalmol Vis Sci.* 2008; 49: 772-80; the contents of which is incorporated herein by reference in its entirety); Purinergic agents—e.g., A2a adenosine receptor agonists (such as CGS21690) (Liu et al., 2008, supra); cAMP agonists—e.g., forskolin (Liu et al., 2008, supra); Phosphodiesterase inhibitors (PDE4 and PDE5 classes)—e.g., rolipram, avanafil, respectively; AMP-activated protein kinase inhibitors—e.g., dorsomorphin dihydrochloride, compound C (Liu et al., 2008, supra); Chloride channel activators—eg, genistein and related flavonoids, benzoflavones; (Caci et al., *Am J Physiol Lung Cell Mol. Physiol.* 2003; 285: L180-8; Galietta et al., *J Biol. Chem.* 2001; 276: 19723-8; Pedemonte et al., *Mol. Pharmacol.* 2005; 67: 1797-1807; Yang et al., *J Biol. Chem.* 2003; 278: 35079-85; the contents of each of which is incorporated herein by reference in its entirety): Others—ascorbate (Martin et al., *J. Neurochem.* 2002; 82: 538-49; the entire contents of which is incorporated herein by reference in its entirety); lithium, sirtuin activators—resveratrol (Grozinger et al., *J Biol. Chem.* 2001; 276: 38837-43; Howitz et al., *Nature.* 2003; 425: 191-6; the contents of each of which is incorporated herein by reference in its entirety).

Compounds Capable of Reducing Ceroid and Lipofuscin from Compromised Lysosomes:

Anti-oxidants—e.g., Vitamin E (Monji et al., *Brain Res.* 1994; 643: 62-8), lipoic acid (Bergamini, 1987, Exp Mol. Pathol. 46(1): 114-22); curcumin (Aoki et al., *Mol. Pharmacol.* 2007; 72: 29-39), acetylhomocysteine thiolactone (Aloj et al., *Arch Geroniol Geriatr.* 1985; 4: 67-72), acetyl-carnitine (Amenta et al., *Arch Gerontol Geriatr.* 1989; 9: 147-53; Spagnoli et al., *Neurology.* 1991; 41: 1726-32); hpofuscinolytics—meclofenoxate, DMAE-p-chlorophenoxyacetate (Riga and Riga *Brain Res.* 1974; 72: 265-75; Zs-Nagy *Arch Gerontol Geriatr.* 1989; 9: 215-29); Ceroid depletors—e.g., phosphocysteamine (Zhang et al., *Nat. Med.* 2001; 7: 478-84); Cathepsin activators—Lipoic acid (Lockwood *Antioxid Redox Signal.* 2002; 4: 681-91); ZPAD (Butler and Bahr, Antioxid Redox Signal. 2006 January-February; 8(1-2):185-96). The entire content of each of the above references is incorporated herein by reference.

Additional Stimulators of Autophagic Protein Turnover (Possible Mechanism Unclear):

diphenylbutyrlpiperidines—e.g., pimozide (Zhang et al., 2007, Proc Natl Acad Sci USA. 104(48): 19023-8); L-type calcium channel blockers—e.g., nicardipine (Zhang et al., 2007, supra); loperamide (Zhang et al., 2007, supra); Vitamin D derivatives (Hoyer-Hansen et al., 2005, Cell Death Differ. 12(10): 1297-309); imidazoline-1 receptor agonists—e.g., rilmenidine (Williams et al., 2008, Nat Chem. Biol. 4(5): 295-305); calpain inhibitors (Williams et al. 2008, supra); rosiglitazone (Han et al., *PPAR Res.* 2007; 2007: 29632); Anti-lipolytic agents—e.g., 3,5'-dimethylpyrazole (Donati et al., 2008, Biochem Biophys Res Commun. 366(3): 786-92). The entire content of each of the above references is incorporated herein by reference.

Compounds will be screened in the cell culture model and assayed for modulation of lysosomal pH, activation of lysosomal hydrolases, and effects on cell viability, run in triplicate as described below:

In Situ Screening Assay of Lysosomal pH in Living Cells:

In a more particular embodiment, quantification of lysosomal pH is determined using Dextran conjugated Lysosensor Yellow/Blue (Invitrogen) as follows. 3000 Wild Type and PS1KO blastocysts were seeded in multiple wells of black, clear bottom tissue culture treated 96 well dish and grown in High Glucose DMEM+15% FBS with antibiotics to ~90% confluency (~24 hours). 2 ul of 0.5 mg/ml lysosensor-dextran (1:100 dilution of a 5 mg/ml stock) was added and incubated for 1 hour at 37° C. with 5% $CO_2$. The cells were then washed 3× in HBSS. See also methods and results set forth herein below in Example 2. This modified protocol represents an optimized protocol for the purposes set forth herein.

In Situ Screening Assay of Cathepsin Activities in Lysosomes of Living Cells:

Identical aliquots of cells grown to a density of at least $5\times10^5$ cells/ml are transferred to wells of a 96 well plate at 37° C. to which is added compounds to be tested in appropriate concentrations for 1 hour.

CatB activity is be measured by adding MR-CatB solution to medium in the wells at a 1:26 dilution of 260× stock solution from manufacture (Immunochemistry Technologies). Active Cat D is labeled by adding Bodipy-FL-pepstatin A (Invitrogen) directly to the medium at a final concentration of 1 µg/ml. Cells are incubated for 15 to 60 minutes at 37° C. under 5% $CO_2$, while protecting from light. 15-20 µl of the cell suspension is added on a 96 well plate and measured with an excitation filter of 550 nm (540-560 nm) and a long pass >610 nm emission/barrier or excitation filter or 485 nm and 535 nm filter equipped plate reader for CatB and CatD, respectively. Measurements are performed in triplicate and negative and positive controls are used as above.

Cytotoxicity Assay:

A 96 well plate containing the identical sets of cells and test compounds incubated under the same conditions is used to measure cell death induced by any compound using the MTS assay as described by the manufacturer (Promega), with appropriate blanks and negative controls.

Intracellular Protein Degradation Measurements:

Compounds showing positive results in one or more assays above will be assessed for effects on total protein degradation by autophagy in cells as measured in pulse-chase experiments (Auteri et al., 1983, supra; the entire contents of which is incorporated herein by reference). These studies, which are routine practice, involve labeling with [$^3$H]-leucine for 48 hrs at 37° C. to preferentially label long-lived proteins. Following labeling, cells are maintained in complete medium (DMEM+ 10% fetal bovine serum), which suppresses autophagy, or in serum-deprived medium, which induces autophagy. Proteolysis is expressed as the percentage of the initial acid-precipitable radioactivity (protein) transformed to acid-soluble radioactivity (amino acids and small peptides) over time.

In vivo testing of promising compounds in AD mouse models is performed as described herein.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Methods and Materials

Cell Lines, Mouse and Reagents

Murine blastocysts with different presenilin (PS1) genotypes (WT, BD6; PS1 KO BD15; PS1/2 KO, BD8) previously characterized by Lai et. al. (2003, J Biol Chem 278, 22475-22481), were used in this study. In addition, human PS1 wt was stably transfected into the BD8 line (Laudon et al., 2004). Human fibroblasts lines, acquired from the Coriell Institute (Camden N.J.), Karolinska Institute (Upsala, Sweden), University di Firenze (Italy) and University of Western Australia (Perth). PS1 hypomorph (Rozmahel et al., 2002) and PS cKO mice (Saura et al., 2004) were studied at 13 month and 2-3 month, respectively, together with age-matched controls.

Intracellular Protein Degradation Measurements

Total protein degradation in cultured cells was measured by pulse-chase experiments (Auteri et al., 1983, supra).

Ultrastructural and Morphometric Analyses and Autophagic Vacuole Isolation and Subcellular Fractionation Following treatments, cells were prepared for EM as previously described and AVs, identified using previous morphological criteria (Yu et al., 2005), were classified and counted on electron micrographs (7900× print magnification) of 20 EM images from different lines in each experimental group and AVs were isolated by centrifugation in a discontinuous metrizamide density gradient (Marzella et al., 1982) for each cell.

Gel Electrophoresis, Immunoblotting and Deglycosylation

Immunoblotting was performed as previously described (Herreman et al., 2003).

Confocal Laser Scanning Microscopy

Immunocytochemistry was performed as previously described (Yu et al., 2005).

Enzymatic Assays

Cathepsin B and L activity were assayed as described previously (Nakanishi et al., 1994, supra) and Cathepsin D activity was assayed using [$^{14}$C]methemoglobin as previously described by Dottavio-Martin and Ravel (1978).

Analytical Procedures

The quantitative colocalization analysis was performed using ImageJ software (NIH Image) with colocalization analysis plugins (Wright Cell Imaging facility). The value shown represents Pearson's coefficient. Statistical analysis was calculated by two-tailed paired student t-test using GraphPad InStat (GraphPad Software Inc.). Error bars represents standard error of the mean (±S.E.M).

Additional methods are described in detail hereinabove.

Results

PS1 Gene Deletion Selectively Inhibits Macroautophagic Turnover of Proteins.

We investigated the competence of proteolytic systems in blastocysts from wild type (WT) mice and constitutive PS1 KO mice using a well-established metabolic labeling procedure (Auteri et al., 1983, supra). Neither incorporation of [$^3$H]-leucine into proteins, used as a measurement of protein synthesis (FIG. 1A), nor proteolysis of short-lived proteins, reflective mainly of ubiquitin-proteasome-dependent degradation (FIG. 1B), were significantly altered in PS1 KO cells. However, the turnover of long-lived proteins was decreased in PS1 KO cells compared to WT under serum-supplemented media (FIG. 1C). When autophagic/lysosomal degradation was induced through serum withdrawal, proteolysis increased 15-20% in WT cells ($p<0.05$) but was not significantly changed in PS1 KO cells (FIG. 1C). Under these induced conditions, inhibiting lysosome-related protein degradation with $NH_4Cl$ (20 mM) entirely blocked the increase of proteolysis in both cell types as expected (FIG. 1D). When macroautophagy was selectively inhibited with 3-methyladenine (3MA, 10 mM) (Seglen and Gordon, 1982), only the increased proteolysis in WT cells was blocked (FIG. 1D), indicating that the residual increase in lysosome-related degradation in response to serum removal in PS1 KO cells is not due to macro autophagy. Together, these findings demonstrate that PS1 deletion selectively affects macroautophagic turnover of proteins.

We next assessed the competence of the nutrient-related signaling pathway leading to mTOR-mediated induction of autophagy. For this, we measured the phosphorylation state of p70S6 kinase (p70S6K), a substrate of mTOR, before and after serum deprivation. Levels of both total p70S6K and its phospho-epitope (Thr389), measured by quantitative immunoblotting analyses, were comparable in WT and PS1 KO cells grown in serum-containing medium (FIG. 1E). Moreover, phospho-p70S6K levels declined comparably in both cell types after inducing autophagy by serum withdrawal for 6 hrs, indicating that mTOR is inhibited normally in response to nutrient deprivation in PS1 KO cells (FIG. 1E).

To evaluate autophagosome formation, we used immunofluorescence labeling with antibodies to LC3. LC3-positive vesicular profiles of sizes 0.5-2.0 µm, were significantly more numerous in PS1 KO cells than in WT cells grown in serum and were slightly increased after serum withdrawal (FIG. 1F,G, $p<0.05$). Consistent with immunocytochemical findings, LC3 western blot analyses showed that ratios of LC3-II to LC3-I, or LC3-II levels alone, were more than 2-fold higher ($p<0.05$) in PS1 KO cells than WT cells grown in the presence of serum. Serum withdrawal resulted in higher LC3-II levels in both WT cells and PS1 KO cells although, in the latter cells, the proportional increase over the already elevated level of LC3-II was less than in WT cells (FIG. 1H). Inducing autophagy by inhibiting mTOR directly with rapamycin yielded similar results.

AVs (autophagosomes, early and late autolysosomes with relatively undigested material and amorphous electron-dense digested materials, respectively) were identified ultrastructurally on the basis of their size and morphology. Autophagosomes and early autolysosomes were more numerous in PS1 KO cells whereas most AVs in WT cells were late autolysosomes. Despite abnormally high baseline AV numbers, PS1 KO cells exhibited modestly elevated AV numbers after serum withdrawal. AVs and lysosomes isolated from cells on metrizamide gradients confirmed that engulfed materials were less degraded in PS1 KO cells compared to WT cells, where most materials were extensively digested, and lysosomes were mainly small and electron-dense, representing a terminal stage of degradation. These data suggested that, in PS1 KO cells, autophagic protein degradation was impaired after fusion with lysosomes.

Defective Clearance of Autophagic Vacuoles in PS1 KO Blastocysts

We next investigated whether PS1 deletion affected the competence of AVs to fuse with lysosomes and late endosomes.

In WT cells, autophagy induction increased the number of LC3-positive vesicles which also co-labeled with antibody markers for lysosomes (LAMP-2) or late endosomes (LBPA). Compared to WT cells, PS1 KO cells under serum supplemented conditions showed a higher degree of LC3 colocalization with either LAMP-2 or LBPA, and remained high after inducing autophagy with rapamycin.

Figure 2:
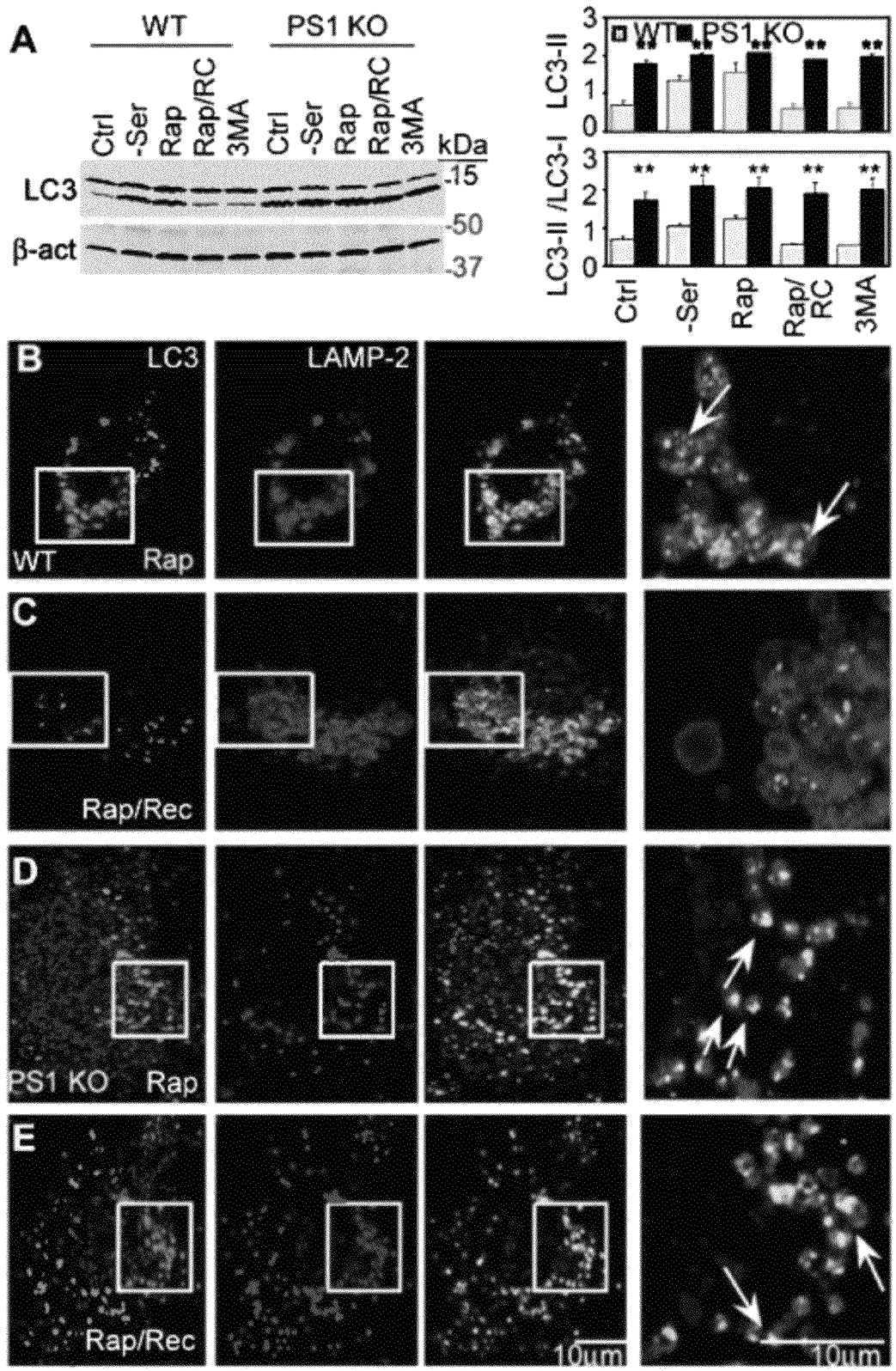
FIG. 2A-E shows impaired clearance of LC3-II from autolysosomes in PS1 KO cells: (A) Immunoblot analysis of LC3-I and -II levels in WT and PS1 KO cells under conditions of no treatment (Ctrl), serum starvation (-Ser), rapamycin (Rap), rapamycin treatment followed by rapamycin removal (Rap/RC), and 3MA. WT (B,C) and PS1 KO cells (D,E) analysed by double-immunofluorescence using LC3 and LAMP-2 antibodies under conditions of rapamycin treatment (B,D) and the later removal of rapamycin (C,E). Right-panels depict enlarged images of the boxed areas seen in the left panels. Quantitative immunoblot analysis of data in (A) is presented graphically as mean±S.E.M. for 3 different experiments. Scale bar represents 10 μm. ** for $p<0.001$.
Figure 3:
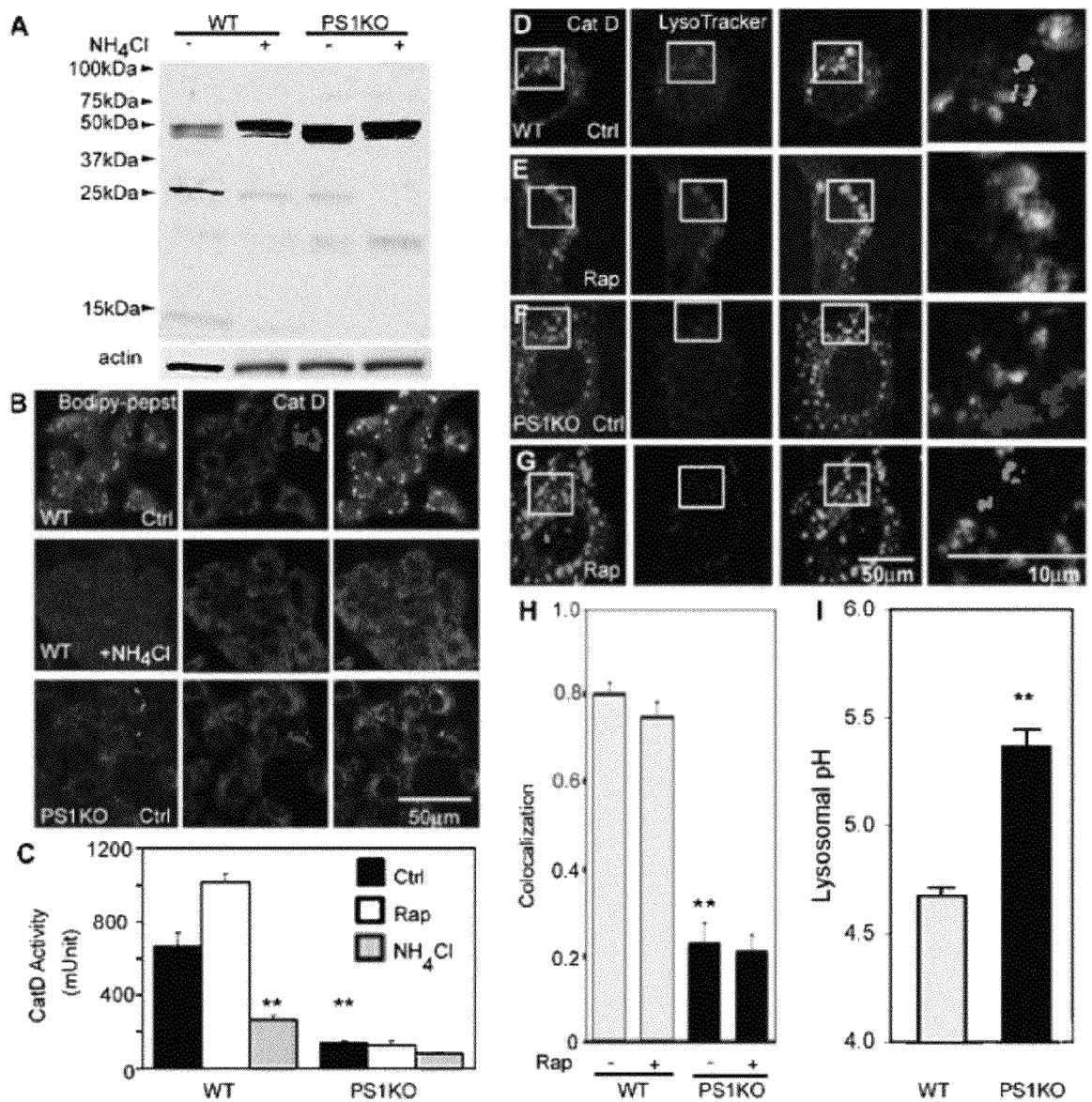
FIG. 3A-I reveals that cathepsin processing and activity are impaired in PS1 KO cells: (A) Cat D immunoblots show reduced generation of the mature two-chain (31 kDa; 14 kDa) form in PS1 KO cells, similar to NH$_4$Cl treated (20 mM; 6 hrs) WT cells. (B) In vivo Cat D activity assays with Bodipy-FL-pepstatin A. After Bodipy-FL-pepstatin A treatment, cells were immunolabeled with Cat D antibody. Bodipy-FL-pepstatin A binds to active Cat D of WT blastocysts and colocalize, but minimal colocalization is shown in PS1 KO cells or WT cells treated with NH4Cl. The scale bar represents 50 mm. (C) In vitro assays of Cat D enzyme activities in WT and PS1 KO cells with or without rapamycin or NH4Cl.  for $p<0.001$. (D-H) Cells with or without rapamycin (10 nM; 6 hr) were preincubated with LysoTracker and immunolabeled with Cat D antibody (D-G). Cat D-positive compartments were LysoTracker-positive in WT cells (D and E) but LysoTracker-negative in PS1 KO cells (F and G). Scale bars represent 50 or 10 mm. (H) Quantitative analysis of LysoTracker and Cat D-positive compartments.  for $p<0.001$. (I) Lysosomal pH values were measured ratiometrically using LysoSensor yellow/blue-Dextran.  for $p<0.001$. Values are shown as means±SEM
Figure 4:
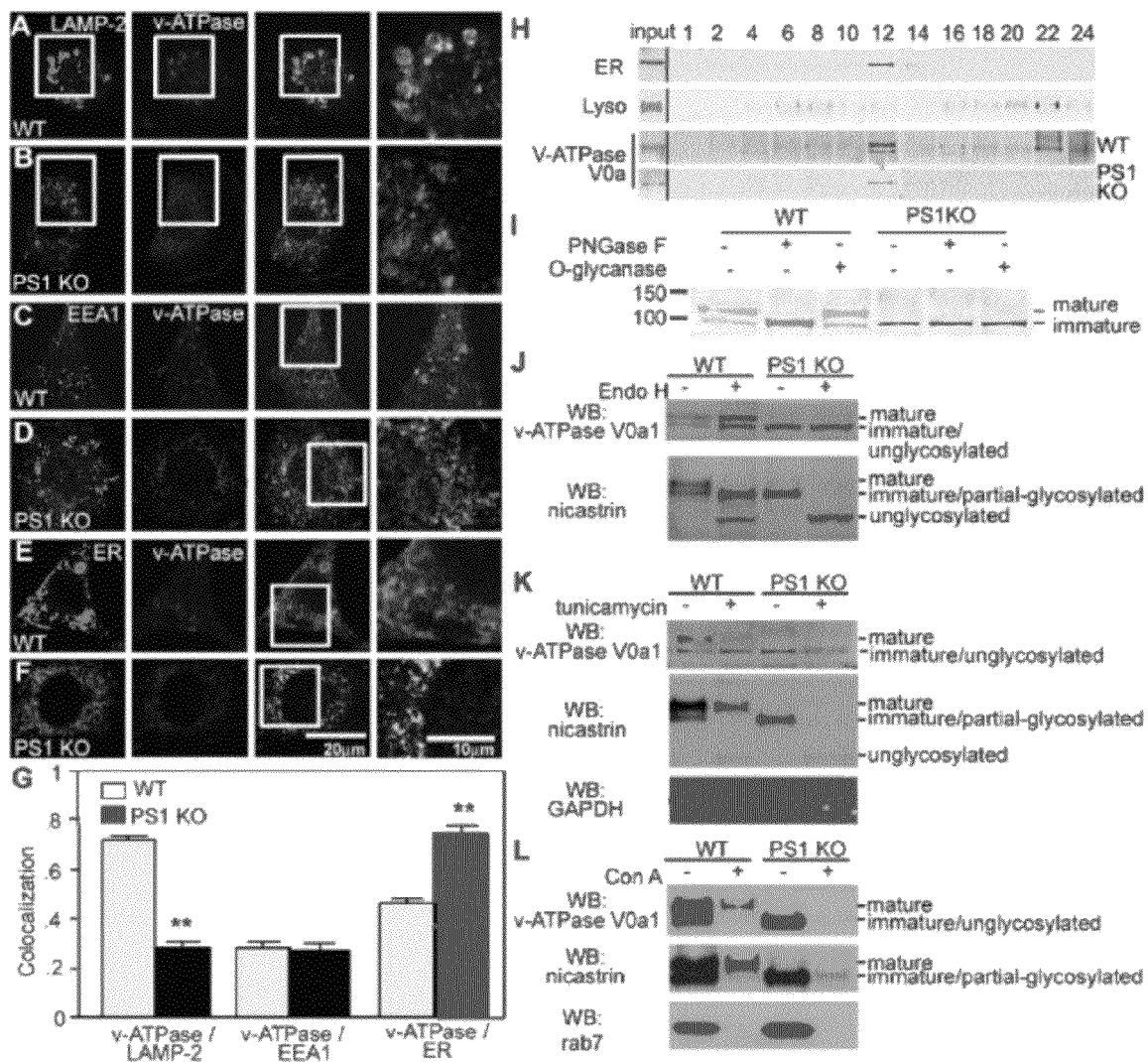
FIG. 4A-L shows that lysosomal targeting of v-ATPase is impaired in PS1 KO blastocysts: Double-immunofluorescence labeling with antibodies to v-ATPase (V0a1 subunit) and LAMP-2 shows strong colocalization in WT cells (A) but minimal colocalization in PS1 KO cells (B). Double labeling with antibodies to v-ATPase (V0a1 subunit) and early endosomal marker, EEA1, shows little colocalization in both WT (C) and PS1 KO cells (D). Co-immunostaining with antibodies to v-ATPase (V0a1 subunit) and the ER marker, calnexin, shows strong co-localization in PS1KO cells (F) but minimal co-localization in WT cells (E). Scale bars represent 20 μm and 10 μm (region of interest). (G) Quantitative analysis of v-ATPase (V0a1 subunit) association with organelle markers. All values are reported as mean±S.E.M. for n=30 cells ( for $p<0.001$). (H) Immunoblot analysis of v-ATPase V0a1 subunit distribution in subcellular fractions of WT and PS1KO cells. Western blot analysis of the fractionation (total lysate pattern provided in lane 1 for comparison) reveals the ER marker, calnexin, primarily located in fraction 12, while the lysosomal marker LAMP2 distributes mainly in fraction 22. In WT cells, the v-ATPase V0a1 subunit, detected as 100 and 120 kDa bands was present in fraction 12 (120 kDa and 100 kDa) and fraction 22 (only in its 120 kDa form), but was primarily detected in the ER-rich fraction (only as a 100 kDa protein) of PS1KO cells. (I) Lysates from WT and PS1KO cells were treated with PNGase F or O-glycanase. The N-glycosylated form of v-ATPase V0a subunit (120 kDa) was deglycosylated (100 kDa) after treatment with PNGase F but not with O-glycanase in WT cells. The v-ATPase V0a1 subunit in PS1 KO cells, by contrast, was not N-glycosylated, with the 100 kDa form unchanged by treatment. (J) Cell lysates were treated with EndoH. Both 100- and 120-kDa band were not sensitive to Endo H in WT cells. This revealed that the 100-kD protein is non-glycosylated core protein and 120-kD protein is complex glycosylated mature protein. EndoH digestion of nicastrin is a positive control. (K) Cells were incubated with tunicamycin to blocks the glycoproteins synthesis in the ER. Resulted in an increase in mobility which 100-kDa in the presence of tunicamycin, compared with 120-kDa in the absence of tunicamycin in WT cells. (L) Cell lysates were incubated with Con A bead and glycoproteins were eluted. Only the 120-kDa v-ATPase V0a1 species were bound, whereas both mature and partial glycosylated nicastrin species binding to Con A column in positive control and Rab7 as a negative control.
Figure 5:
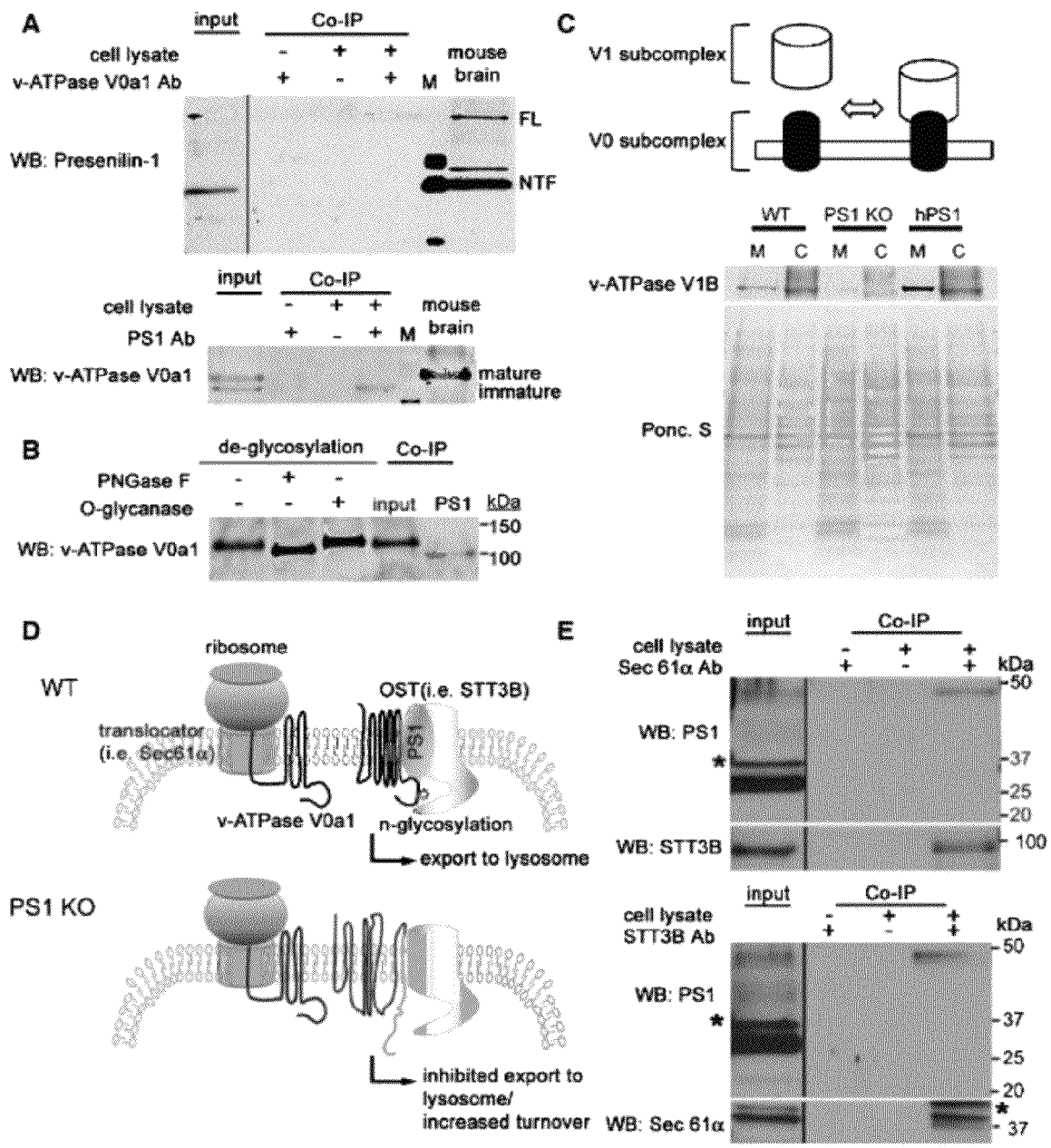
FIG. 5A-E shows that PS1 directly binds to the v-ATPase V0a subunit and affects its maturation and the assembly of the v-ATPase complex: (A) Co-immunoprecipitation of endogenous PS1 with anti-v-ATPase V0a1 antibody and v-ATPase V0a1 with anti-PS1-NTF antibody. Whole cell lysate was incubated and precipitated with the Seize primary immunoprecipitation kit. Precipitated proteins were detected by immunoblot with either anti-PS1 (Ab14) or anti-v-ATPase V0a1. M represents the marker lane. (B) Lysate from WT mouse brain was treated with PNGase F or O-glycanase. The v-ATPase V0a1 subunit is highly glycosylated in mouse brain. The N-glycosylated form of v-ATPase V0a1 subunit (120 kDa) is deglycosylated, as evidenced by a molecular weight shift to 100 kDa after treatment with PNGase F but not with O-glycanase. The v-ATPase V0a1 subunit was immunoprecipitated with anti-PS1-NTF antibody and detected by anti-v-ATPase V0a1 antibody. Only unglycosylated v-ATPase V0a1 subunit co-precipitates with PS1. (C) The diagram in the top panel shows a model of v-ATPase assembly. Immunoblot analysis of the v-ATPase V1B subunit shows distributions between the membrane and cytosolic fractions. (D) The diagram shows a hypothetical model of N-glycosylation of the v-ATPase V0a1 subunit via PS1. PS1 binding to translocon and OST complex can then facilitate the presentation of v-ATPase V0a1 subunit to the OST complex. (E) Co-precipitation of endogenous PS1 with anti-Sec61α antibody and STT3B antibody. Only full length PS1 was co-precipitated with Sec61α and STT3B. Sec61α and STT3B were also co-immunoprecipitated each other. * represent non-specific band.

Further analyses of autolysosome maturation showed that clearance of LC3 after fusion, a measure of autophagy degradative competence, was greatly impaired in PS1 KO cells. In WT cells, acute autophagy induction with rapamycin elevated LC3-II levels by immunoblot analysis. These levels returned to pretreatment baseline levels within 6 hrs after removing rapamycin from the medium; however, in PS1 KO cells, LC3 levels remained significantly elevated (FIG. 2A). Double-immunofluorescence labeling with LC3 and LAMP-2 antibodies confirmed that LC3 accumulated in LAMP-2-positive vesicles after rapamycin exposure of WT (FIG. 2B) and PS1 KO cells (FIG. 2D), but 6 hrs after rapamycin was removed, LC3 was nearly completely eliminated from these vesicles only in WT cells, and not in PS1 KO cells (FIG. 2C,E). Despite this evidence that autophagosomes can fuse with lysosomes, inspection at higher magnification revealed that LC3 distributed more peripherally along the membrane of the fused vesicles in PS1 KO cells compared with those in WT cells, suggesting that the handling of LC3 after autophagosome-lysosome fusion is impaired (FIG. 2, compare B and D).

Using an alternative approach to investigate autophagosome clearance, we observed that LC3 levels remained abnormally high in PS1 KO cells even when autophagosome formation was blocked for 6 hrs with 3MA (FIG. 2A). Moreover, treatment with leupeptin (0.3 mM, 6 hrs) to inhibit cysteine proteases in autolysosomes, significantly elevated LC3-II levels and LC3-positive puncta in WT cells, but in PS1 KO cells, this treatment did not increase LC3 levels beyond the elevated baseline evident in these cells before leupeptin addition. As an alternative assessment of LC3-II turnover, p62/SQSTM1 degradation may also be used to evaluate impairments of autophagic protein degradation (Bjorkoy et al., 2005). In addition to LC3-II accumulation, p62 levels also increased in PS1 KO cells. Each of these three lines of evidence consistently supports a defect in autophagic vacuole clearance.

Proteolysis Deficits in Autolysosomes of PS1 KO Blastocysts

We investigated further the basis for delayed clearance of LC3 and other autophagy substrate proteins by examining the activation of cathepsins in PS1 KO cells. Western blot analyses of Cathepsin D (CatD), the major aspartyl protease of lysosomes, showed slightly elevated total Cat D immunoreactivity levels but a more rapid migration of the mature single chain enzyme on gels than the WT enzyme (46 kDa) and decreased proteolytic generation of 31- and 14-kDa forms of the mature enzyme in PS1 KO cells (FIG. 3A). This deficit was similar to that seen in WT cells when lysosomal pH was neutralized by treatment with $NH_4Cl$ (Isidoro et al., 1991) or Bafilomycin A1. Metabolic labeling data confirmed that Cat D maturation was impaired in PS1 KO cells. To assess Cat D activation within lysosomes, we incubated cells with Bodipy-FL-pepstatin A, which binds selectively to active Cat D (Chen et al., 2000). Dual fluorescence analyses of WT cells using Cat D antibodies showed strong double-labeling of compartments with Cat D antibodies and Bodipy-FL-pepstatin A, which was nearly completely abolished when lysosomal pH was neutralized by treatment with $NH_4Cl$. By contrast, in PS1 KO cells, Bodipy-FL-pepstatin A labeling within Cat D-positive vesicles was markedly reduced despite normal numbers of these compartments (FIG. 3B). To analyze Cat B activity in vivo, we used MR-Cat B, a cresyl-violet conjugated (Arg-Arg)$_2$ peptide, which fluoresces only after it is cleaved by Cat B in an acidic environment. We confirmed that, in PS1 KO cells, MR-CatB signal was dramatically reduced compared to WT and was similar to levels seen in WT cells in which lysosomal acidification was inhibited using $NH_4Cl$ (Figure S4D). In vitro assays of Cat D activity in PS1 KO cells in the absence or presence of rapamycin confirmed a markedly reduced proteolytic activity relative to WT cells (FIG. 3C). The activities of the cysteine proteases Cat B and Cat L were also similarly lowered in PS1 KO cells under these conditions. Similar or more severe reductions in cathepsins B, D, and L activities were achieved in WT cells by incubating them in the presence of $NH_4Cl$ (FIG. 3C).

Defective Lysosome Acidification in PS1 KO Blastocysts

The possibility that lysosome acidification may be impaired, raised by the foregoing observations, was further investigated by evaluating another process requiring lysosome acidification, namely, the dissociation of the cation-independent mannose-6-phosphate receptor (CI-MPR) from cathepsins after their delivery to late endosomes. Using double-immunofluorescence labeling with antibodies to Cat D and CI-MPR, we observed that most Cat D-positive vesicles were CI-MPR-negative in WT cells, but were nearly all CI-MPR-positive in PS1 KO cells, indicating that dissociation of CI-MPR from Cat D was impaired. CI-MPR co-immunoprecipitation with Cat D data revealed more Cat D bound to CI-MPR in PS1 KO cells, a phenomena reversed by human PS1 reintroduction. To assess lysosome acidification directly, we used LysoTracker, an acidotropic dye which strongly fluoresces in acidic environments. In WT cells, LysoTracker demonstrated strong fluorescence in virtually all Cat D-positive vesicles (FIG. 3D), while in PS1 KO cells, fewer than 20% of Cat D-positive vesicles exhibited detectable fluorescence (FIG. 3F,G). Compared to that in WT cells, LysoTracker signal in PS1 KO cells remained low after inducing autophagy with rapamycin (FIG. 3J,G,H). Using LysoSensor yellow/blue DND-160-Dextran, we quantified lysosomal pH was significantly elevated in PS1 KO cells (5.4±0.08) compare to WT cells (4.7±0.04) ($p<0.0001$) (FIG. 3I). Double-immunofluorescence labeling with LC3 and LysoTracker confirmed that nearly all LC3-positive compartments were not fully acidified in PS1 KO cells.

Impaired Glycosylation and Targeting of the v-ATPase V0a1 Subunit in PS1 KO Cells To further understand the basis for the acidification defect in PS1 KO cells, we investigated the v-ATPase V0a1 subunit as a marker of proton pump function in lysosomes. Double-immunofluorescence labeling analysis revealed strong co-localization of v-ATPase with LAMP-2-positive compartments in WT cells (FIG. 4A). In PS1 KO cells, however, v-ATPase immunolabeling was concentrated in a perinuclear region remote from most of the peripherally distributed LAMP-2-positive compartments (FIG. 4B). v-ATPase immunoreactivity strongly colocalized with calnexin, an ER-integral protein, in PS1KO cells (FIG. 4F) but minimally in WT cells (FIG. 4E). As expected, colocalization of v-ATPase with EEA1 (early endosome antigen-1) was nearly absent in early endosomes of both WT and PS1KO cells (FIG. 4C,D). Quantitative analyses of marker colocalization showed a significantly greater extent of association of v-ATPase with ER than with lysosomes in PS1KO cells, converse to the pattern seen in WT cells (FIG. 4G). Subcellular fractionation studies confirmed the immunocytochemical results showing that v-ATPase was retained in the ER-rich (calnexin-positive) fraction but was markedly depleted from the lysosomal (LAMP2) fraction in PS1 KO cells, whereas in WT cells, v-ATPase was enriched in both ER and lysosomal fractions (FIG. 4H).

In subcellular fractions from PS1 KO cells, we also observed that the v-ATPase V0a1 subunit located in ER-enriched fractions exists as a single 100 kDa band, whereas, in WT cells, it was present as a double band (120/100 kDa) in the ER enriched fraction and as a single 120 kDa band in the lysosome-enriched fraction. Further studies in which we deglycosylated v-ATPase V0a1 subunits from cell lysates with either PNGase F or O-glycanase revealed that the 100 kDa protein is the non-N-glycosylated immature form and that the 120 kDa protein is the N-glycosylated mature form (FIG. 4I). To further determine the state of v-ATPase V0a1 maturation, cells were incubated with tunicamycin (N-linked glycosylation inhibitor) (FIG. 4J) or cell lysate were either treated with the Endo H (FIG. 4K) or performed affinity binding studies using concanavalin A (Con A) lectin column (FIG. 4L). These lines of evidence revealed that the 110-kD protein is non-glycosylated core protein and 120-kD protein is complex glycosylated mature protein.

To investigate a possible role of PS1 in v-ATPase V0a1 subunit maturation, we performed co-immunoprecipitation assays with the endogenous proteins from WT cells and mouse brain. Precipitation of endogenous v-ATPase V0a1 subunit led to co-precipitation of full length PS1 but not its more abundant N or C terminal cleavage products, indicating that only full length PS1 can bind to the v-ATPase V0a1 subunit (FIG. 5A, top). Importantly, PS1 preferentially co-precipitated with the immature 100 kDa form of v-ATPase V0a subunit (FIG. 5A, bottom). In WT mouse brain, only unglycosylated immature v-ATPase bound to PS1 even though a large proportion of the v-ATPase V0a1 subunit pool in this tissue was N-glycosylated (FIG. 5B). These data indicated that uncleaved PS1 binds to immature v-ATPase V0a1 to modulate its maturation in the ER and effect delivery to lysosomes.

The v-ATPase is a multicomplex molecule composed of a membrane bound V0 subcomplex and a cytosolic V1 subcomplex and is only active when both subcomplexes are assembled in the lysosomal membrane. We next examined the v-ATPase multicomplex assembly status using membrane fractionation. Relatively small amounts of the v-ATPase V1B subunit were present in the membrane fraction and negligible amounts were detected in the cytosolic fraction in PS1 KO cells relative to WT cells (FIG. 5C). This observation shows that PS1 deletion alters v-ATPase assembly and that the unassembled V1 subunit normally detectable in the cytosol is depleted and presumably degraded in PS1 KO cells.

If PS1 is solely responsible for these deficits in autolysosome function, exogenously reintroduced PS1 should be able to rescue the PS1 KO phenotype. To test this, we used human PS1 (hPS1) stably expressed PS KO cells. The hPS1 introduction restored strong LysoTracker fluorescence of vesicular compartments in these cells. Moreover, western blot analyses showed that the 31 kDa mature form of Cat D and the mature form of v-ATPase V0a reappeared in hPS1 cells. Blastocysts from mice in which both PS1 and PS2 were deleted (PS1/2 KO) exhibited macroautophagy deficiencies comparable to those of PS1 KO cells; however, stable transfection of human PS1 into PS1/2 KO cells completely restored macroautophagy responses, as evidenced by the increases in protein degradation in response to serum deprivation and the restoration of a normal percentage of 3-MA-sensitive proteolysis in these cells. These data strongly support the conclusion that, under conditions of PS1 ablation, the v-ATPase V0a1 subunit is not N-glycosylated and, therefore, is retained in the ER, thereby preventing acidification of lysosome-related compartments and activation of proteases in autolysosomes during autophagy.

We suspected that PS1 may be involved in N-glycan transfer from the oligosaccharyltransferase (OST) to the v-ATPase V0a1 subunit after its translation and translocation via the translocon (FIG. 5D). Supporting this mechanism, co-immunoprecipitation data showed that endogenous full length PS1 preferentially co-precipitates with Sec61α (translocon subunit) and STT3B (OST subunit) (FIG. 5E) and vice versa, however other ER protein such as GRP94 and PDI did not interact. These data support a mechanism in which full length PS1 holds the v-ATPase V0a1 subunit close to the OST complex, thereby facilitating posttranslational N-glycosylation of the subunit (FIG. 5D).

Defective Vesicle Acidification and Autophagic Pathology in Neurons of PS1 Hypomorphic and PS cKO Mice.

Figure 6A:
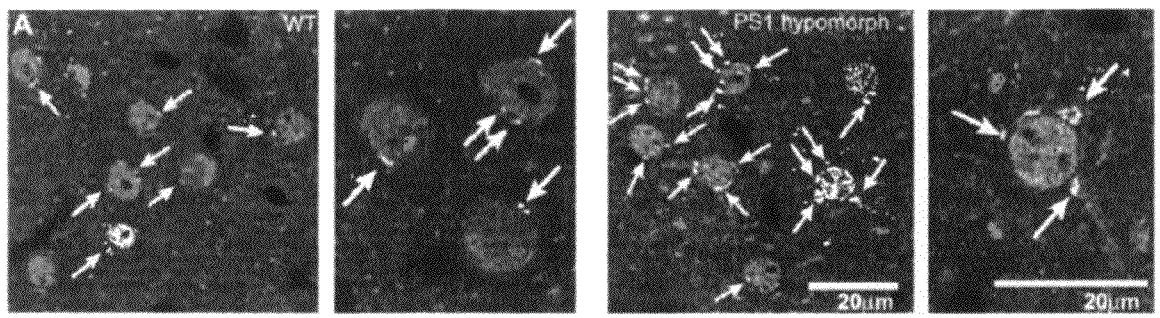
FIG. 6A-D depicts defective autophagosome accumulation and acidification in PS1 hypomorphic mice. (A) LC3 immunohistochemistry of PS1 hypomorph brain shows greater LC3 staining (arrow) in the PS1-deficient mouse compared to the WT. The scale bar represents 20 mm. (B) EM of AVs and dystrophic neurite-like structures in brains of PS1 hypomorph mice compared to littermate controls. The scale bar represents 500 nm. (C) Quantitation of AVs per EM field.  for $p<0.001$. (D) DAMP, a marker which localizes to acidic compartments, was infused intraventricularly into the brains of mice and analyzed by immuno-EM with dinitrophenol (DNP; 10 nm-gold, arrowheads) and CatD (6 nm-gold, arrows) antibodies. Graphs show quantitation of immunogold labeling for DAMP and CatD.  for $p<0.001$. All values are means±SEM.
Figure 6B:
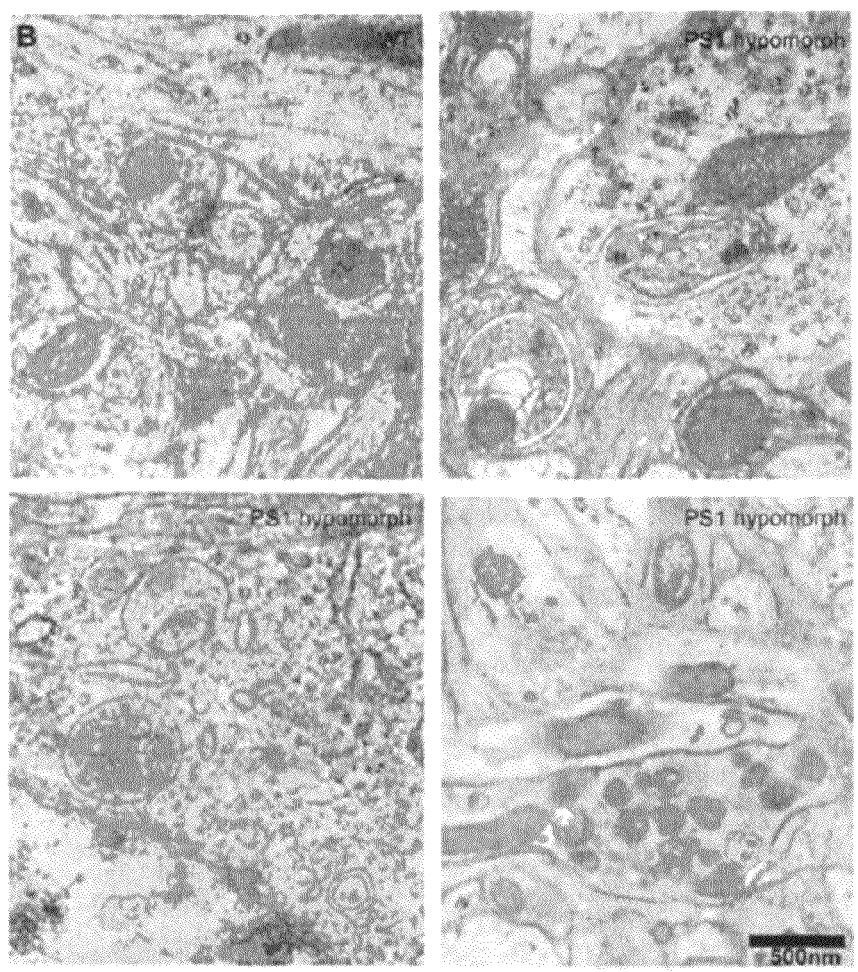
Figure 6C:
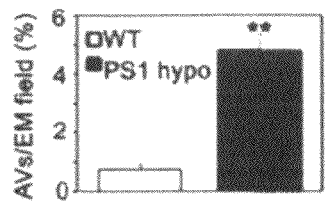
Figure 6D:
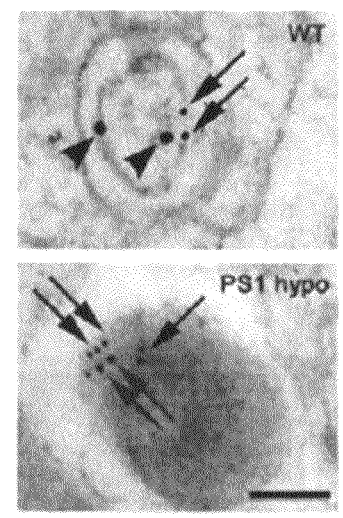
Figure 6D:
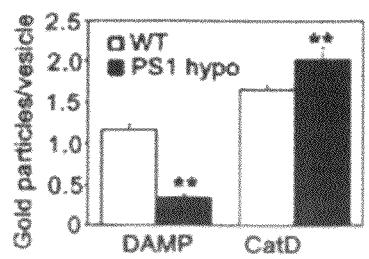
Figure 7:
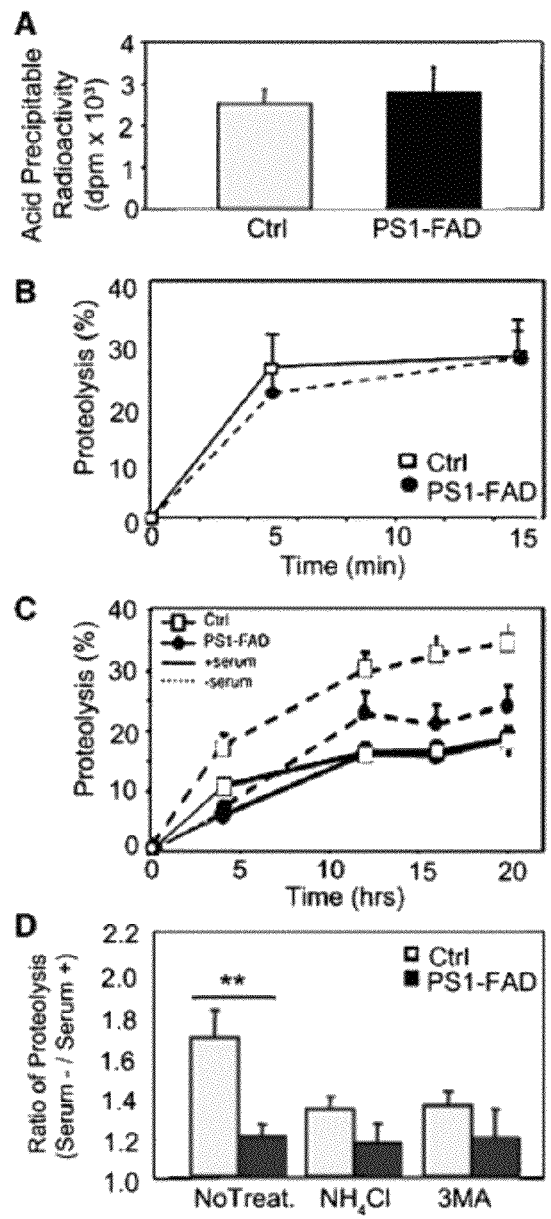
FIG. 7A-F shows defective autophagy in PS1-FAD human fibroblasts. (A) Fibroblasts from five different PS1-FAD patients and age matched controls were incubated with [$^3$H]-leucine and the incorporation of radiolabeled leucine to proteins (protein synthesis) were calculated. (B) Following labeling with [$^3$H]-leucine, the proteolysis of short-lived proteins in the same cells was measured following the chase period. (C) Degradation of long-lived proteins was measured in control and [$^3$H]-FAD fibroblasts cells after incorporation of [$^3$H]-leucine followed by incubation in serum-supplemented or -deprived medium during the chase period (up to 20 hrs) (* for $p<0.05$, n=15). (D) The increase in proteolysis at 12 hrs after removal of serum relative to serum-replete conditions was determined for control and PS1-FAD fibroblasts cells that were treated with $NH_4Cl$ (20 mM) or 3MA (10 mM) ( for $p<0.001$, n=15), with untreated cells as their control. All values are the mean±S.E.M. (E) Increase in the degradation of long-lived proteins after serum removal was compared in fibroblasts from control (n=11) and PS1-FAD patients carrying different PS1 mutations (as labeled). Each graphical point corresponds to triplicate measurements for each cell line. The mean value of the different cell lines with the same mutation is indicated as a black line and the increase in proteolysis within the control group following serum deprivation is indicated as a dotted line across the panel. (F) Control or PS1-FAD fibroblasts treated in the absence of serum were preincubated with LysoTracker and immunolabeled for LAMP-1. LAMP-1-positive compartments colocalized with LysoTracker control cells, but not in PS1-FAD, as verified by quantitative analysis).  for $p<0.001$. Values are shown as means±SEM.
Figure 7:
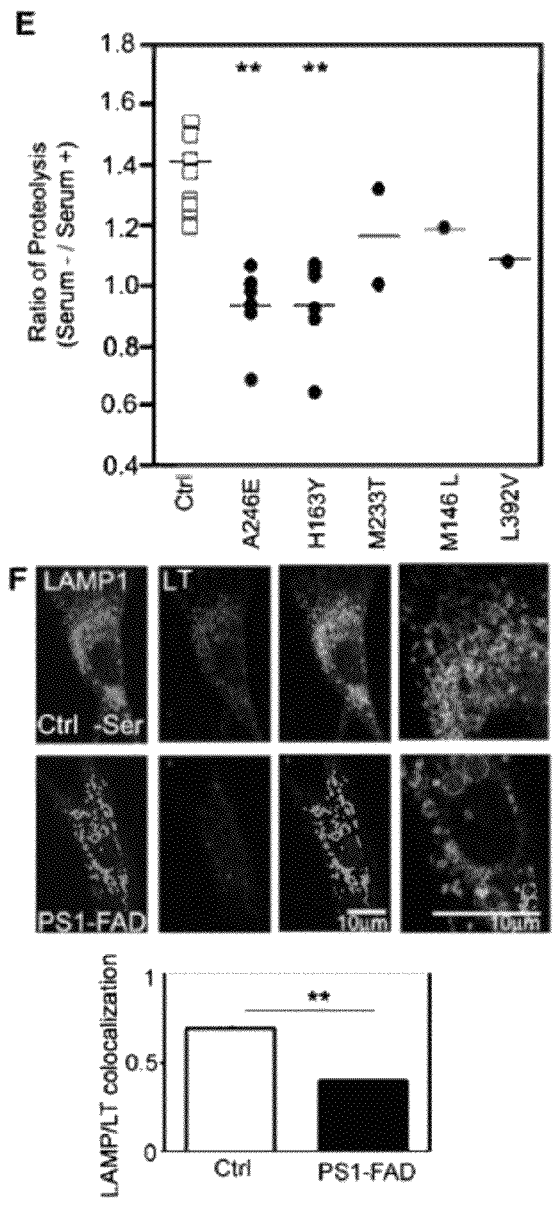

To extend these observations to neurons in vivo, we examined whether AVs accumulate in association with defective lysosome acidification in mouse models of PS1 hypofunction. PS1 hypomorphic mice expressing very low levels of PS1 protein (1%) but sufficient for brain development and normal lifespan, displayed significantly increased numbers of LC3-positive compartments in neurons of the cortex and hippocampus (FIG. 6A) and 6-fold higher numbers of immature AVs ($p<0.0001$) quantified by EM morphometry compared to the corresponding numbers in WT mice (FIG. 6B). To assess lysosome acidification in vivo in these mice, we performed intraventricular injections of DAMP, a probe sensitive to changes in vesicular pH (Anderson et al., 1984) followed by double-immunogold EM using antibodies to CatD to identify lysosome-related vesicles and dinitrophenol to detect the presence of DAMP, the abundance of which reflects the degree of acidification of the compartments (Anderson et al. 1984). These data showed that vesicle acidification was much less in Cat D-positive compartments in neurons of PS1 hypomorph mice than in WT controls (FIG. 6B, bottom). Similarly, PS cKO mice, under conditions of PS1 conditional knockdown, exhibited abnormally increased numbers of LC3-positive compartments and AV in brain (FIG. 6C) and significantly decreased acidification of lysosomal compartments compared to WT controls ($p<0.0001$) (FIG. 6D). These results confirm that the PS1-dependent lysosomal acidification defect observed in the cell culture system also occurs in vivo in the brain of PS1-deficient mice.

PS1 Mutations Impair Macroautophagy and v-ATPase Targeting in Fibroblasts from Patients with Familial AD PS1-FAD and control human fibroblasts exhibited comparable rates of [$^3$H]-leucine incorporation into proteins (FIG. 7A), degradation of short-lived proteins (FIG. 7B), and proteolysis of long-lived proteins under autophagy-suppressed conditions (FIG. 7C). By contrast, when macroautophagy was induced by serum withdrawal, PS1-FAD fibroblasts exhibited a minimal rise in proteolysis compared to control fibroblasts. NH$_4$Cl treatment eliminated the difference in proteolytic rates between the two cell groups (FIG. 7D), confirming that proteolysis impairment selectively involved the lysosomal system in PS1-FAD fibroblasts. In an expanded analysis, including a total of 16 different PS1-FAD lines sub-classified by the specific PS1 mutation (A246E, M233T, H163Y, M146L, L392V), autophagic protein degradation was lowered compared to the control cells (FIG. 7E). The LC3-II/LC3-I ratio and also total LC3-II levels in PS1-FAD fibroblasts were also comparatively high even in serum supplemented conditions and stayed elevated compared to control cells after serum removal (FIG. 7F). To reassess autophagosome formation, control and PS1-FAD fibroblasts were immunostained with LC3 antibody, which revealed increased LC3 vesicular puncta in PS1-FAD compared to control fibroblasts after autophagy was induced by serum withdrawal (FIG. 7G). Morphometric ultrastructural analyses revealed that immature AVs were more numerous in PS1-FAD cells than in control fibroblasts where the AVs were mainly smaller and electron-dense, representing a terminal stage of autophagic degradation (FIG. 7H). We also confirmed using LysoTracker that the level of acidification of the lysosomal compartments (highlighted with LAMP-1) in PS1-FAD was markedly lower (FIG. 7I).

To investigate the mechanism underlying impaired autophagic protein turnover in PS1 FAD fibroblasts, we use a double-tagged mRFP-GFP-LC3 construct, which enabled us to assess lysosome acidification in living cells in vitro. Almost all of the RFP and GFP signal colocalised in PS1 FAD fibroblasts under serum starved conditions indicating that acidification of lysosomes is insufficient to quench GFP fluorescence or, less likely, transport of mRFP-GFP-LC3 to acidic compartments (i.e. lysosome) is delayed. By contrast, in control fibroblasts, only 10% of green fluorescent vesicles also contained RFP signal, indicating that formation of acidified autolysosomes is efficient. Accumulation of p62 immunoreactivity before or after serum starvation was disproportionately high in PS1 FAD fibroblasts by western blot analysis or by ICC analysis of p62 localization within LC3-positive compartments, consistent with delayed proteolytic autolysosomal clearance of this autophagy-selective substrate. Double-immunofluorescence labeling with V0a1 antibodies established that the v-ATPase was localized with CatD-positive compartments in control fibroblasts, but only a small proportion of v-ATPase colocalized with Cat D in PS1 FAD fibroblasts. To investigate v-ATPase targeting further in PS1 FAD fibroblasts, we conducted double labeling studies with antibodies to v-ATPase and the ER marker PDI, which revealed that most v-ATPase immunoreactivity colocalized with calnexin in PS1 FAD fibroblasts but not control fibroblasts, as confirmed quantitatively. Additional double-label analyses showed that the v-ATPase V0a1 subunit also colocalized less with V1B1/2 subunit in PS1 FAD fibroblasts compared to control cells. Also v-ATPase amount was decreased in PS1 FAD fibroblast.

DISCUSSION

Our results identify a novel, essential role of PS1 in lysosomal-dependent proteolysis directly relevant to the mechanism by which PS1 mutations accelerate the pathogenesis of AD. PS1 deletion prevented macroautophagic protein turnover while minimally affecting non-lysosomal turnover of short and long-lived proteins. We have traced this defect in autophagy-dependent proteolysis to inadequate autolysosome/lysosome acidification resulting from failure of the V0 subunit of v-ATPase to become N-glycosylated in the ER and subsequently delivered to autolysosomes/lysosomes. This acidification defect explains the many other abnormalities of AV dynamics and autolysosome maturation/digestion that we and others have observed in PS1 KO cells (Wilson et al., 2004; Esselens et al., 2004). Furthermore, we also demonstrate that neurons in the brains of mouse models of PS1 hypofunction and cells of patients with AD caused by PS1 mutations show similar autolysosome maturation defect. Lysosomal acidification is necessary to dissociate CI-MPR from cathepsins, complete the proteolytic maturation of cathepsin D, and activate cathepsins (Kokkonen et al., 2004). All of these functions were impaired in PS1 KO cells, resulting in delayed proteolytic clearance of autophagic substrates and their accumulation in autophagic vacuoles. Transfection of WT hPS1 into PS1/2 KO cells rescued all of these deficits.

Earlier studies reported that impaired turnover of telencephalin and α-synuclein in PS1 KO cells (Wilson et al., 2004; Esselens et al., 2004) accompanied appearance of these proteins in autophagic compartments, indicating that their turnover by autophagy may be defective; however, the specificity of proteolytic defects for autophagy relative to other proteolytic systems and the molecular mechanism underlying PS1-related effects on autophagy were not defined. Here we show that these proteolytic defects are selective for lysosome-dependent proteolysis, that these deficits are also present in neurons of PS1-depleted mice, and that AD-related mutations of PS1 cause a substantial loss of the same lysosomal/autophagic functions that are more severely disrupted in PS1-null cells. Our findings indicate that impaired turnover of telencephalin and α-synuclein is a reflection of a general defect in macroautophagic proteolysis rather than a specific problem in the turnover of these particular substrates (Esselens et al., 2004). In addition, we have shown for the first time that the proteolytic deficits in PS1 KO cells are selective for lysosomal turnover because non-lysosomal turnover of short and long-lived proteins was minimally affected.

Multiple lines of evidence in our study established that defective autophagy in PS1 KO cells principally reflects a failure to degrade autophagy substrates and clear AVs due to a specific defect in lysosome/autolysosome acidification. This evidence in PS1 KO cells includes, abnormally elevated levels of autophagy substrates (p62, LC3), a failure to clear AVs formed after rapamycin-mediated autophagy induction, the minimal effect of a cathepsin inhibitor (leupeptin) on LC3-II accumulation in PS1 KO cells, impaired maturation of cathepsin D, reduced specific activities of multiple cathepsins in vitro and in situ within lysosomes, and impaired dissociation of MPR from cathepsins. Impaired degradation in PS1 KO cells is also indicated by the high proportions of early autolysosomes compared to electron-dense late autolysosomes in morphometric analyses and the low recovery of dense lysosomes in subcellular fractionations. All of these effects are expected outcomes of a defect in the acidification of autolysosomes/lysosomes, which was demonstrated directly by the marked decrease of LysoTracker fluorescence, DAMP labeling and by the very low abundance of the V0a1 subunit of v-ATPase in lysosome-related compartments. Similar kinds of deficits have been observed when v-ATPase is inhibited with bafilomycin (Yoshimori et al., 1991) or when vacuolar acidification is blocked with ammonium chloride (Contento et al., 2005).

In contrast to these striking effects on autophagic proteolysis, PS1 deletion did not detectably alter major upstream aspects of macroautophagy, including nutrient-dependent regulation of mTOR, a protein kinase-signaling pathway that utilizes AKT-P13K (Sarbassov et al., 2005) and is modulated in part by presenilin 2 (Kang et al., 2005). In response to autophagy induction, p70S6 kinase was normally dephosphorylated and LC3-positive puncta and AVs increased modestly but significantly above an already elevated level in PS1 KO cells, indicating preservation of an ability to form autophagosomes. The accumulation of p62, a known autophagy substrate (Bjorkoy et al., 2005), indicated that PS1 KO cells can sequester substrates despite the subsequent impairment of degradation. The presence of LC3/LAMP2-positive profiles in PS1 KO cells is evidence of autophagosome-late endosome fusion as seen by Wilson et al. (2004), but not by Esselens et al. (2004), and is consistent with other evidence that autophagosome-lysosome fusion is not dependent on lysosomal acidification (Jahreiss et al., 2008), although we cannot rule out that the fusion rate might be slower in the presence of impaired AV clearance. Other key aspects of lysosomal biogenesis and function were also not detectably unaltered in PS1 KO cells, such as the delivery of cathepsins and LAMPs to late endosome/lysosomes and the distribution and levels of rab7 required for lysosome maturation (Bucci et al., 2000). Thus, the failure of v-ATPase targeting to lysosomes is a relatively selective effect of PS1 deletion on proteolytic steps in the autophagy pathway.

The v-ATPases are multisubunit complexes which are composed of a membrane-bound subcomplex V0 and a cytosolic V1 subcomplex (Forgac, 2007). We established that PS1 physically associates with the unglycosylated, immature form of v-ATPase V0a1 subunit, which enables the N-glycosylation required for this subunit to be efficiently exported from the ER and delivered to lysosomes (Gillespie et al., 1991; Nishi and Forgac, 2002). This is not a generalized effect on the N-glycosylation mechanism itself since Lamp2 is normally glycosylated in PS1KO cells. N-glycosylation occurs on ER membranes where oligosaccharyltransferase (OST) transfers a $Glc_3Man_9GlcNAc_2$ to a target protein exiting from translocon pores (Kelleher and Gilmore, 2006) (FIG. 5D). Co-immunoprecipitation data show that full length PS1 preferentially co-precipitated with Sec61α (translocon) and STT3B (OST complex). Our findings implicating PS1 holoprotein provide an explanation for the observation in an earlier study (Esselens et al., 2004) and confirmed here that the influences of PS1 and PS1 deletion on autophagy are not dependent on γ-secretase activity. This conclusion is supported by our observation that deletion of nicastrin in blastocysts or treatment of these cells with a γ-secretase inhibitor had no effect on lysosomal acidification or autophagic protein turnover.

Our findings on fibroblasts from patients with AD caused by PS1 mutations demonstrated substantial lysosomal/autophagy deficits arising from the same disruption of v-ATPase trafficking and lysosomal acidification that cause the more severe deficits in PS1 KO blastocysts. The neuropathology of AD is characterized by profuse accumulations of autophagic vacuoles in swollen dystrophic neurites throughout affected brain regions (Nixon et al., 2005), consistent with impaired or delayed autophagosome clearance (Boland et al., 2008). These autophagy defects as well as amyloidogenesis and neuronal cell death are accelerated by mutations of PS1 (Cataldo et al., 2004). Our data, therefore, account for the accelerated lysosomal system-driven pathology in this familial form of AD and likely contribute to the lowered neuronal cell viability seen in PS-FAD relative to sporadic AD (Mattson et al., 2000) since autophagy is required for neuronal survival (Hara et al., 2006; Komatsu et al., 2006).

In conclusion, our studies define a novel essential role for PS1 in the maturation and trafficking of the v-ATPase responsible for lysosome acidification. We have demonstrated the adverse consequences of ablating this function for the normal turnover of proteins and organelles by autophagy. It is likely that a failure of PS1-dependent v-ATPase trafficking would have a range of additional effects on functions of other compartments that rely on this proton pump to acidify the intralumenal environment.

REFERENCES

Anderson, R. G. W., Falck, J. R., Goldstein, J. L., and Brown, M. S. (1984). Visualization of Acidic Organelles in Intact Cells by Electron Microscopy. Proc Natl Acad Sci 81, 4838-4842.

Auteri, J. S., Okada, A., Bochaki, V., and Dice, J. F. (1983). Regulation of intracellular protein degradation in IMR-90 human diploid fibroblasts. J Cell Physiol 115, 167-174.

Bjorkoy, G., Lamark, T., Brech, A., Outzen, H., Perander, M., Overvatn, A., Stenmark, H., and Johansen, T. (2005). p62/SQSTM1 forms protein aggregates degraded by autophagy and has a protective effect on huntingtin-induced cell death. J Cell Biol 171, 603-614.

Boland, B., Kumar, A., Lee, S., Platt, F. M., Wegiel, J., Yu, W. H., and Nixon, R. A. (2008). Autophagy Induction and Autophagosome Clearance in Neurons: Relationship to Autophagic Pathology in Alzheimer's Disease. J Neurosci 28, 6926-6937.

Cataldo, A. M., Peterhoff, C. M., Schmidt, S. D., Terio, N. B., Duff, K., Beard, M., Mathews, P. M., and Nixon, R. A. (2004). Presenilin mutations in familial Alzheimer disease and transgenic mouse models accelerate neuronal lysosomal pathology. J Neuropathol Exp Neurol 63, 821-830.

Chen, C.-S., Chen, W.-N. U., Zhou, M., Arttamangkul, S., and Haugland, R. P. (2000). Probing the cathepsin D using a BODIPY FL-pepstatin A: applications in fluorescence polarization and microscopy. Journal of Biochemical and Biophysical Methods 42, 137-151.

Citron, M., Westaway, D., Xia, W., Carlson, G., Diehl, T., Levesque, G., Johnson-Wood, K., Lee, M., Seubert, P., Davis, A., et al. (1997). Mutant presenilins of Alzheimer's disease increase production of 42-residue amyloid beta-protein in both transfected cells and transgenic mice. Nat Med 3, 67-72.

Contento, A. L., Xiong, Y., and Bassham, D. C. (2005). Visualization of autophagy in Arabidopsis using the fluorescent dye monodansylcadaverine and a GFP-AtATG8e fusion protein. The Plant Journal 42, 598-608.

Cuervo, A. M., Stefanis, L., Fredenburg, R., Lansbury, P. T., and Sulzer, D. (2004). Impaired degradation of mutant α-synuclein by chaperone-mediated autophagy. Science 305, 1292-1295.

De Strooper, B., Saftig, P., Craessaerts, K., Vanderstichele, H., Guhde, G., Annaert, W., Von Figura, K., and Van Leuven, F. (1998). Deficiency of presenilin-1 inhibits the normal cleavage of amyloid precursor protein. Nature 391, 387-390.

Dottavio-Martin, D., and Ravel, J. (1978). Radiolabeling of proteins by reductive alkylation with [14C]formaldehyde and sodium cyanoborohydride. Anal Biochem 87, 562-565.

Esselens, C., Oorschot, V., Baert, V., Raemaekers, T., Spittaels, K., Serneels, L., Zheng, H., Saftig, P., De Strooper, B., Klumperman, J., et al. (2004). Presenilin 1 mediates the turnover of telencephalin in hippocampal neurons via an autophagic degradative pathway. J Cell Biol 166, 1041-1054.

Forgac, M. (2007). Vacuolar ATPases: rotary proton pumps in physiology and pathophysiology. Nat Rev Mol Cell Biol 8, 917-929.

Gillespie, J., Ozanne, S., Tugal, B., Percy, J., Warren, M., Haywood, J., and Apps, D. (1991). The vacuolar H(+)-translocating ATPase of renal tubules contains a 115-kDa glycosylated subunit. FEBS Lett 282, 69-72.

Hara, T., Nakamura, K., Matsui, M., Yamamoto, A., Nakahara, Y., Suzuki-Migishima, R., Yokoyama, M., Mishima, K., Saito, I., Okano, H., et al. (2006). Suppression of basal autophagy in neural cells causes neurodegenerative disease in mice. Nature 441, 885-889.

Herreman, A., Van Gassen, G., Bentahir, M., Nyabi, O., Craessaerts, K., Mueller, U., Annaert, W., and De Strooper, B. (2003). γ-Secretase activity requires the presenilin-dependent trafficking of nicastrin through the Golgi apparatus but not its complex glycosylation. J Cell Sci 116, 1127-1136.

Isidoro, C., Horst, M., Baccino, F. M., and Hasilik, A. (1991). Differential segregation of human and hamster cathepsin D in transfected baby-hamster kidney cells. Biochem J 273 (Pt 2), 363-367.

Jahreiss, L., Menzies, F. M., and Rubinsztein, D. C. (2008). The itinerary of autophagosomes: From peripheral formation to kiss-and-run fusion with lysosomes. Traffic 9, 574-587.

Junichi, S., Anastasios, G., Pankaj, M., Zen, K., Claudia, M. L., Lia, B., and Nikolaos, K. R. (2007). FAD mutants unable to increase neurotoxic Aβ42 suggest that mutation effects on neurodegeneration may be independent of effects on Aβ. Journal of Neurochemistry 101, 674-681.

Kelleher, D. J., and Gilmore, R. (2006). An evolving view of the eukaryotic oligosaccharyltransferase. Glycobiology 16, 47R-62.

Kim, T. W., and Tanzi, R. E. (1997). Presenilins and Alzheimer's disease. Curr Opin Neurobiol 7, 683-688.

Klionsky, D. J. (2007). Autophagy: from phenomenology to molecular understanding in less than a decade. Nat Rev Mol Cell Biol 8, 931-937.

Kokkonen, N., Rivinoja, A., Kauppila, A., Suokas, M., Kellokumpu, I., and Kellokumpu, S. (2004). Defective Acidification of Intracellular Organelles Results in Aberrant Secretion of Cathepsin D in Cancer Cells. J Biol Chem 279, 39982-39988.

Komatsu, M., Waguri, S., Chiba, T., Murata, S., Iwata, J., Tanida, I., Ueno, T., Koike, M., Uchiyama, Y., Kominami, E., et al. (2006). Loss of autophagy in the central nervous system causes neurodegeneration in mice. Nature 441, 880-884.

Lai, M. T., Chen, E., Crouthamel, M. C., DiMuzio-Mower, J., Xu, M., Huang, Q., Price, E., Register, R. B., Shi, X. P., Donoviel, D. B., et al. (2003). Presenilin-1 and presenilin-2 exhibit distinct yet overlapping gamma-secretase activities. J Biol Chem 278, 22475-22481.

Laudon, H., Mathews, P. M., Karlstrom, H., Bergman, A., Farmery, M. R., Nixon, R. A., Winblad, B., Gandy, S. E., Lendahl, U., Lundkvist, J., et al. (2004). Co-expressed presenilin 1 NTF and CTF form functional gamma-secretase complexes in cells devoid of full-length protein. J Neurochem 89, 44-53.

Marzella, L., Ahlberg, J., and Glaumann, H. (1982). Isolation of autophagic vacuoles from rat liver: morphological and biochemical characterization. J Cell Biol 93, 144-154.

Mattson, M. P., Zhu, H., Yu, J., and Kindy, M. S. (2000). Presenilin-1 mutation increases neuronal vulnerability to focal ischemia in vivo and to hypoxia and glucose deprivation in cell culture: involvement of perturbed calcium homeostasis. J Neurosci 20, 1358-1364.

Mizushima, N. (2007). Autophagy: process and function. Genes Dev 21, 2861-2873.

Nakanishi, H., Tominaga, K., Amano, T., Hirotsu, I., Inoue, T., and Yamamoto, K. (1994). Age-Related Changes in Activities and Localizations of Cathepsins D, E, B, and L in the Rat Brain Tissues. Experimental Neurology 126, 119-128.

Naruse, S., Thinakaran, G., Luo, J. J., Kusiak, J. W., Tomita, T., Iwatsubo, T., Qian, X., Ginty, D. D., Price, D. L., Borchelt, D. R., et al. (1998). Effects of PS1 deficiency on membrane protein trafficking in neurons. Neuron 21, 1213-1221.

Nishi, T., and Forgac, M. (2002). The vacuolar (H+)-ATPases—nature's most versatile proton pumps. Nat Rev Mol Cell Biol 3, 94-103.

Nixon, R. A., Wegiel, J., Kumar, A., Yu, W. H., Peterhoff, C., Cataldo, A., and Cuervo, A. M. (2005). Extensive involvement of autophagy in Alzheimer disease: An Immuno-Electron Microscopy Study. J Neuropathol Exp Neurol 64, 113-122.

Ravikumar, B., Vacher, C., Berger, Z., Davies, J. E., Luo, S., Oroz, L. G., Scaravilli, F., Easton, D. F., Duden, R., O'Kane, C. J., et al. (2004). Inhibition of mTOR induces autophagy and reduces toxicity of polyglutamine expansions in fly and mouse models of Huntington disease. Nat Genet. 36, 585-595.

Rozmahel, R., Huang, J., Chen, F., Liang, Y., Nguyen, V., Ikeda, M., Levesque, G., Yu, G., Nishimura, M., Mathews, P., et al. (2002). Normal brain development in PS1 hypomorphic mice with markedly reduced γ-secretase cleavage of betaAPP. Neurobiol Aging 23, 187-194.

Rubinsztein, D. C. (2006). The roles of intracellular protein-degradation pathways in neurodegeneration. Nature 443, 780-786.

Samari, H. R., and Seglen, P. O. (1998). Inhibition of Hepatocytic Autophagy by Adenosine, Aminoimidazole-4-carboxamide Riboside, and N6-Mercaptopurine Riboside. J Biol Chem 273, 23758-23763.

Saura, C. A., Choi, S. Y., Beglopoulos, V., Malkani, S., Zhang, D., Shankaranarayana Rao, B. S., Chattarji, S., Kelleher, R. J., 3rd, Kandel, E. R., Duff, K., et al. (2004). Loss of presenilin function causes impairments of memory and synaptic plasticity followed by age-dependent neurodegeneration. Neuron 42, 23-36.

Schmelzle, T., and Hall, M. N. (2000). TOR, a Central Controller of Cell Growth. Cell 103, 253-262.

Seglen, P. O., and Gordon, P. B. (1982). 3-Methyladenine: specific inhibitor of autophagic/lysosomal protein degradation in isolated rat hepatocytes. Proc Natl Acad Sci USA 79, 1889-1892.

Shen, J., and Kelleher, R. J., III (2007). The presenilin hypothesis of Alzheimer's disease: Evidence for a loss-of-function pathogenic mechanism. Proceedings of the National Academy of Sciences 104, 403-409.

Yamamoto, A., Tagawa, Y., Yoshimori, T., Moriyama, Y., Masaki, R., and Tashiro, Y. (1998). Bafilomycin A1 prevents maturation of autophagic vacuoles by inhibiting fusion between autophagosomes and lysosomes in rat hepatoma cell line, H-4-II-E cells. Cell Struct Funct 23, 33-42.

Yoshimori, T., Yamamoto, A., Moriyama, Y., Futai, M., and Tashiro, Y. (1991). Bafilomycin A1, a specific inhibitor of vacuolar-type H(+)-ATPase, inhibits acidification and protein degradation in lysosomes of cultured cells. J Biol Chem 266, 17707-17712.

Yu, W. H., Cuervo, A. M., Kumar, A., Peterhoff, C. M., Schmidt, S. D., Lee, J.-H., Mohan, P. S., Mercken, M., Farmery, M. R., Thernberg, L. O., et al. (2005). Macroautophagy—a novel β-amyloid peptide-generating pathway activated in Alzheimer's disease. J Cell Biol 171, 87-98.

Zhang, J., Kang, D. E., Xia, W., Okochi, M., Mori, H., Selkoe, D. J., and Koo, E. H. (1998). Subcellular distribution and turnover of presenilins in transfected cells. J Biol Chem 273, 12436-12442.

Example 2

Methods and Materials

Lysosomal pH

Quantification of lysosomal pH was determined using Dextran conjugated Lysosensor Yellow/Blue (Invitrogen). 3000 Wild Type and PS1KO blastocysts were seeded in multiple wells of black, clear bottom tissue culture treated 96 well dish and grown in High Glucose DMEM+15% FBS with antibiotics to ~90% confluency (~24 hours). 2 ul of 0.5 mg/ml lysosensor-dextran (1:100 dilution of a 5 mg/ml stock) was added and incubated for 1 hour at 37° C. with 5% $CO_2$. The cells were then washed 3× in HBSS.

pH Calibration

Performed according to the protocol established by Diwu et al (supra). Briefly, wild type and PS1KO blastocysts were treated with 10 uM monensin and 10 uM nigericin in MES buffer (5 mM NaCl, 115 mM KCL, 1.3 mM $MgSO_4$, 25 mM MES), with the pH adjusted to a range from 3.5-7.0 for 7-10 min prior to lysosensor addition (the additional hour in the buffer seems to have no effect), these cells are not washed in HBSS since permeabilization with ionophores makes them susceptible to detachment.

Quantification

The samples were read in a Wallac Victor 2 fluorimeter (Perkin Elmer) with excitation at 355 nm. The ratio of emission 440 nm/535 nm was then calculated for each sample. pH values were determined from the linear std curve generated via the pH calibration samples.

Method of Detecting Neurodegenerative Disease Related Changes in Lysosomal Function Active Cat D was labeled by adding Bodipy-FL-pepstatin A directly to the medium at a final concentration of 1 mg/ml for 1 hr. Following 4% PFA fixation, cells were counter stained with Cat D antibody for 4 hr and visualized with Alexa Fluor 568 conjugated secondary antibody. For assessing Cat B activation, MagicRed-Cathepsin B (Immunochemistry Technologies) for active Cat B was added to the cells at the concentration suggested by the company (1:260). Cells were incubated for 30 min with MR-Cathepsin B prior to mounting them under the confocal microscope. Cat B staining with MagicRed-Cathepsin B was also measured fluorometrically with a Wallac Victor 2 fluorometer.

Results

The signal of MR-Cat B, a fluorescent substrate of CatB that only fluoresces upon cleavage by the active enzyme, is abundantly evident in WT cells but is minimal in PS1 KO cells, similar to that in $NH_4Cl$ treated WT cells. DIC images are depicted visualizing cells. Scale bar represents 50 mm.

A Class of Putative Therapeutic Compounds that Reverse PS (AD) Related Changes in Lysosomal pH and Function Methods The following sets forth a protocol for investigating β-adrenergic agonists as lead candidate therapeutic agents to enhance autophagic-lysosomal degradative efficiency in patient cells, primary neurons, and mouse models of AD.

Rationale, Overall Strategy, and Preliminary Results

The present inventors and their colleagues have previously demonstrated the therapeutic effects of augmenting lysosomal proteolysis in TgCRND8 mice [Yang et al. Brain, 2011. 134(Pt 1): p. 258-77; the entire contents of which is incorporated herein by reference in its entirety]. In a separate approach, the present inventors have now shown that elevated lysosomal pH in PS1 KO cells is restored by the β-adrenergic agonists isoproterenol and clenbuterol to normal levels or even hyperacidic levels, whereas the β-antagonist alprenolol or α-adrenergic agonist phenylepherine did not affect lysosomal pH. Also, in PS1KO cells, isoproterenol (200 µM, 6 h) restored to WT levels: a) lysosomal pH; b) Cat B activity as measured by MR-Cat B; and reversed c) LC3 puncta accumulation determined by LC3 ICC, d) p62 accumulation and e) AV accumulation by EM morphometry [total area occupied by AVs per EM field (≈1 cell per field)]. Clenbuterol possesses particularly desirable properties as β-agonist compound for use in therapeutic applications for human AD patients because it has a good safety profile, has the desired consequences on lysosomal pH and autophagy in PS1-deleted cells at clinically relevant concentrations, and has been used in humans for other indications.

Research Methods

Elucidating the Pathway Through which β-Adrenergic Stimulation Alters Lysosomal pH and Enables AV Clearance:

Clenbuterol and other β-adrenergic agonists in the cAMP/PKA pathway will be tested (eg, forskolin, an adenylyl cyclase activator and rolipram, a specific inhibitor of PDE4 as positive controls) and cAMP levels will be monitored by ELISA (Abcam). PKA activation will be assessed using a non-toxic dose of H-89 [Chijiwa et al. J Biol Chem, 1990. 265(9): 5267-72; the content of which is incorporated herein by reference in its entirety] (as determined by MTS assay) and confirmed via WB against both phospho (active) and whole PKA protein. PI3K activation is assessed using LY294002 [Vlahos et al. J Biol Chem, 1994. 269(7): 5241-8; the content of which is incorporated herein by reference in its entirety] and inhibition of AKT phosphorylation by WB. To implicate non-proton ionic species in the mechanism of lysosomal pH rescue, cells will be pretreated with the ionophore valinomycin to block active ion transport across lysosomes. This should eliminate lysosomal pH restoration by clenbuterol, if it is occurring by altering ion transporter regulation. The possible involvement of TRPML1, a lysosomal Ca2+ channel [Xu et al. Proc Natl Acad Sci USA, 2007. 104(46): 18321-6; the content of which is incorporated herein by reference in its entirety] in the mechanism is tested by pre-treating with verapamil prior to β-adrenergic agonist addition. Should TRPML1 be implicated in this pathway, we can directly monitor Ca2+ levels using commercial fluorogenic substrates, which include dextran conjugated Fura-2 among others, allowing Ca2+ levels to be analyzed in the lysosome. Should CLC-7, and by extension, Cl− be important, we will directly assay the level of lysosomal Cl− by monitoring the endocytic uptake and fluorescent intensity of the Cl− indicator SPQ (Invitrogen) as per Verkman [Verkman et al. Am J Physiol, 1990. 259(3 Pt 1): C375-88; the content of which is incorporated herein by reference in its entirety]. TRPML1 and CLC-7 protein levels will be measured by Western blot with anti-TRPML1 and anti-CLC7 antibodies (Abcam). Since no specific inhibitors of CLC-7 exist, we will use CLC-7 siRNA knock down prior to drug treatment with clenbuterol and the in situ assays described above, an experiment that will also be performed on TRPML1. Furthermore we cannot rule out the influence of additional ionic transport in pH regulation of the lysosome, as both Na+ and K+ flux have been demonstrated in the lysosome, although the exact transporters and exact role in pH regulation remain unclear [Moriyama. Biochem Biophys Res Commun, 1988. 156(1): p. 211-6; Orlowski et al. Curr Opin Cell Biol, 2007. 19(4): 483-92; the contents of each of which is incorporated herein by reference in its entirety]. Therefore, utilization of a generic K+ channel inhibitor or a Na+ channel inhibitor may provide useful data in determining what is occurring at the lysosome after β-adrenergic treatment. Although unlikely based on our preliminary data, restoration of vATPase activity as a contribution to rescue will be tested using techniques in Lee et al. [Cell, 2010. 141: 1146-58; the content of which is incorporated herein by reference in its entirety] to measure possible restoration of vATPase levels.

Figure 8:
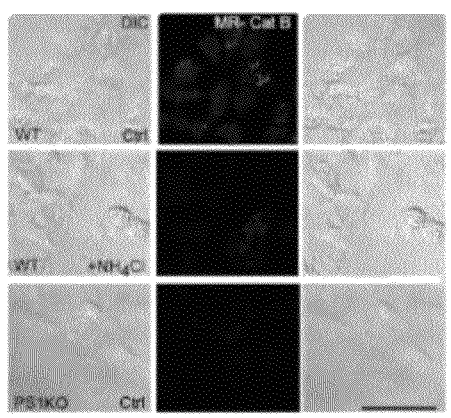
FIG. 8 depicts a panel of immunofluoresence and differential interference contrast (DIC) images showing CatB staining in WT and PS1KO using MR-CatB. MR-Cat B signal is abundantly evident in WT cells but is minimal in PS1 KO cells, similar to that in NH4Cl treated WT cells. DIC images are depicted to aid in visualizing cells. Scale bar represents 50 mm.
Figure 9A:
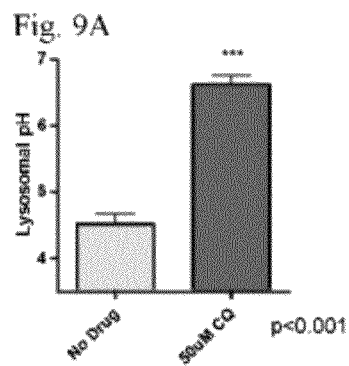
FIG. 9A-D presents a series of histogram graphs that demonstrate validation of lysosomal pH measurement method.
Figure 9B:
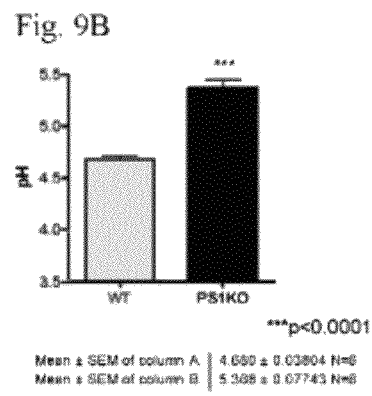
Figure 9C:
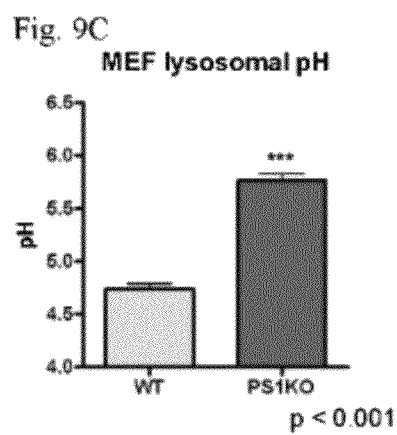
Figure 9D:
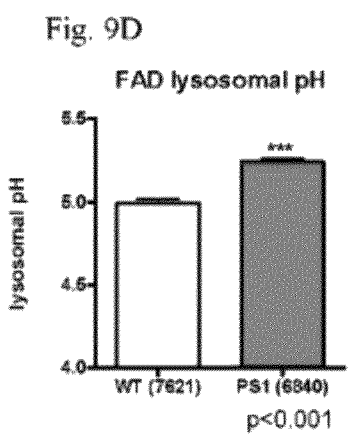

In Situ Assays in Living Cells:

Because the present inventors are interested in both restoring normal pH and possibly enhancing acidity, since this has been associated with enhanced lysosomal proteolysis [Martin et al. J Neurochem, 2002. 82(3): 538-49; the content of which is incorporated herein by reference in its entirety], both normal control fibroblasts and PS1KO cells will be used and any key compounds will be also validated as disease-relevant in human PS1 FAD fibroblasts [Donoviel et al. Genes Dev, 1999. 13(21): 2801-10; Lai et al. J Biol Chem, 2003. 278(25): 22475-81; the contents of each of which is incorporated herein by reference in its entirety] representing the authentic disease-related model of lysosome acidification defects, and also in other FAD cell models, patient fibroblasts and primary neurons from AD models when autophagy and/or transport deficits are confirmed. As described herein, confirmation may be acquired by determining lysosomal pH, which is quantified using lysosensor DND-160 [Liu et al. Invest Ophthalmol V is Sci, 2008. 49(2): 772-80; the content of which is incorporated herein by reference in its entirety], and in vivo activity of Cat B and D may be measured with MagicRed-Cat B and Bodipy-FL-pepstatin A, respectively (as depicted in FIGS. 3B and 8). Promising compounds will also assessed for effects on total and autophagy-specific protein degradation in pulse-chase experiments [Auteri et al. J Cell Physiol., 1983. 115: 167-174; the content of which is incorporated herein by reference in its entirety].

Also under investigation is a novel photoswitchable reporter for the quantification of bulk autophagy rates, as currently used in the Cuervo lab [Subach et al. Nat Chem Biol, 2009. 5(2): 118-26; the content of which is incorporated herein by reference in its entirety] to assess autophagy stimulatory effects of drugs, which involves transduction with a lentiviral vector carrying pPS-CFP2 (Evogen) [Martinez-Vicente et al. J Clin Invest, 2008. 118(2): 777-88; the content of which is incorporated herein by reference in its entirety], photoactivation by a 405 nm light emitting diode (LED: Norlux), which photoconverts all pPS-CFPs from a blue to a green protein. The ratio of photoswitched protein (green; ex: 450 nm em: 532) to the de novo synthesized protein (blue; ex: 350 nm em: 450 nm) is measured over time as reflecting the rate of degradation of the photoconverted protein. Appropriate inhibitors distinguish contributions from different forms of autophagy and non-lysosomal proteolysis.

Additional Test Compounds:

In addition to isoproterenol and clenbuterol, screens of additional β-adrenergic compounds of various subclasses have been use to identify other potent agents and further confirm the specificity of the receptor mechanism. Also, further definition of the ion transporter(s) involved in rescue will give leads to additional compounds with pH modulatory effects. A range of concentrations of test compounds will be tested above and below a clinically or physiologically relevant concentration. In addition to the effects of compounds that function, at least in part, through β-adrenergic receptor activation, other compounds of utility operating through the same or different mechanisms likely exist. For example, we find that resveratrol and nicardipine, a sirtuin activator and Ca2+ channel blocker, respectively, are capable of partially restoring active Cat B in PS1 KO cells. Having performed a rational screen as originally proposed, we have a series of additional compounds of interest beyond the β-adrenergic agonists.

At the outset, the validity of the method described herein to measure lysosomal pH is confirmed. See, for example, FIG. 9A-D. More particularly, to assess the validity of the method of quantifying lysosomal pH, WT blastocysts were treated with chloroquine (CQ), which is known to elevate lysosomal pH. As seen in the FIG. 9A, CQ significantly elevated WT lysosomal pH. Utilizing this method, as described in Lee et al. [Cell, 2010. 141: 1146-58; the content of which is incorporated herein by reference in its entirety], lysosomal pH was measured in WT and PS1KO blastocysts, with PS1KO demonstrating a significantly more alkaline lysosomal pH. See, for example, FIG. 9B. This phenomenon was confirmed in multiple cell lines, including mouse embryonic fibroblasts (MEFs) and patient derived fibroblasts (FAD). See, for example, FIGS. 9C and D, respectively.

Figure 10A:
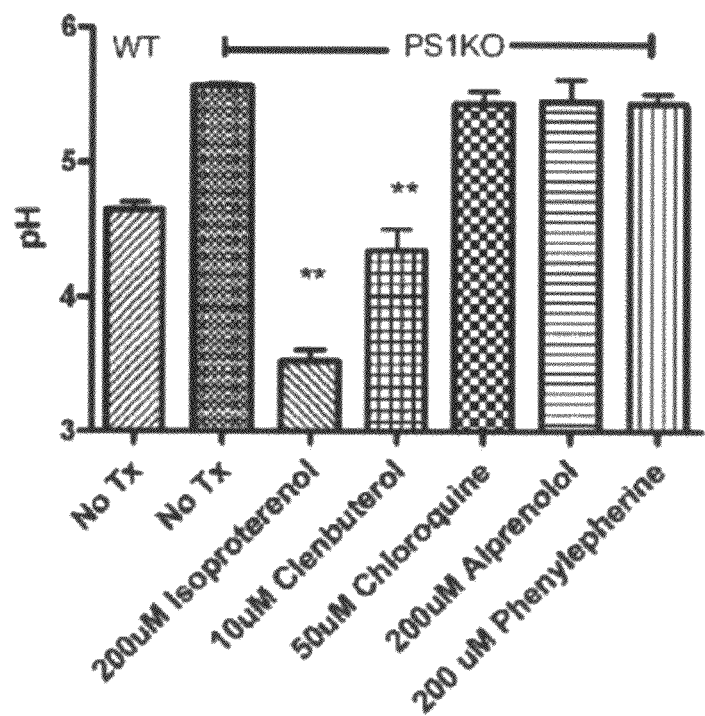
Figure 10A:
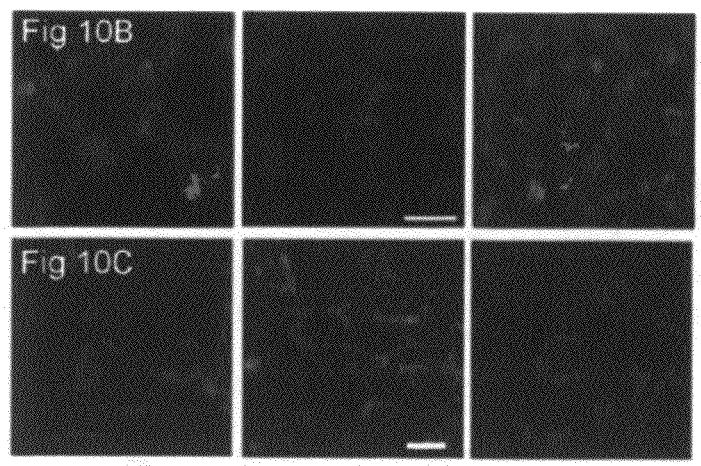
Figure 10E:
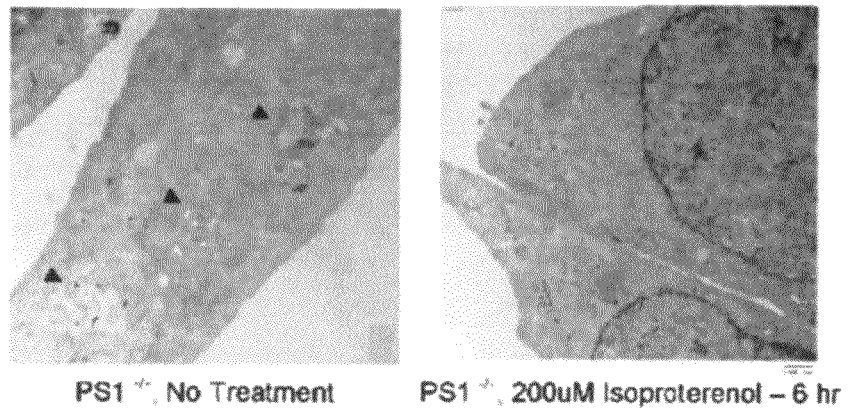
Figure 10E:
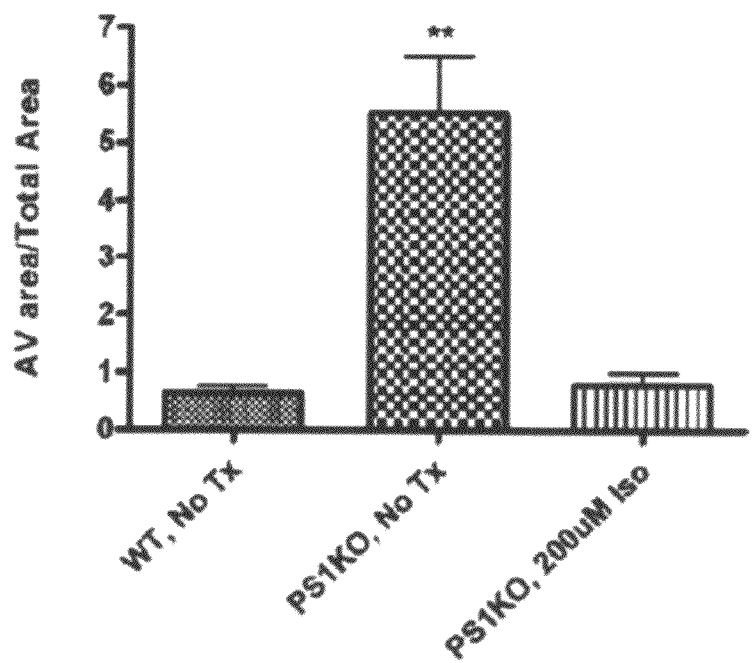
Figure 10F:
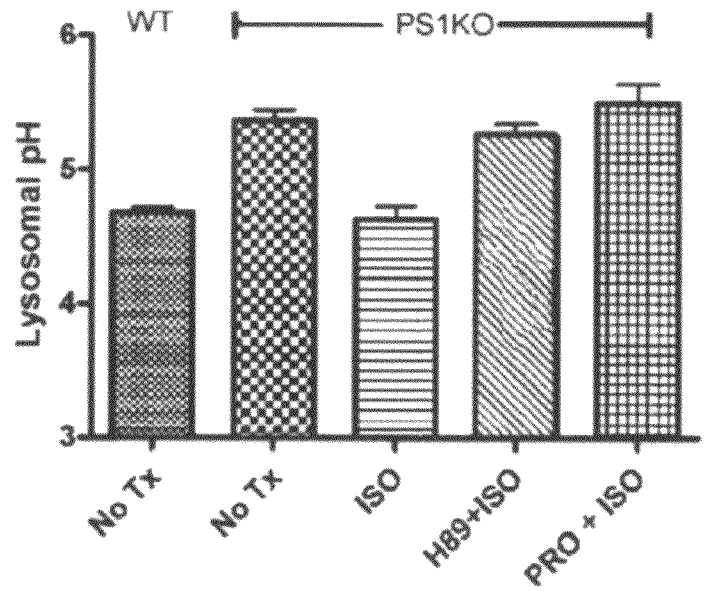
Figure 10G:
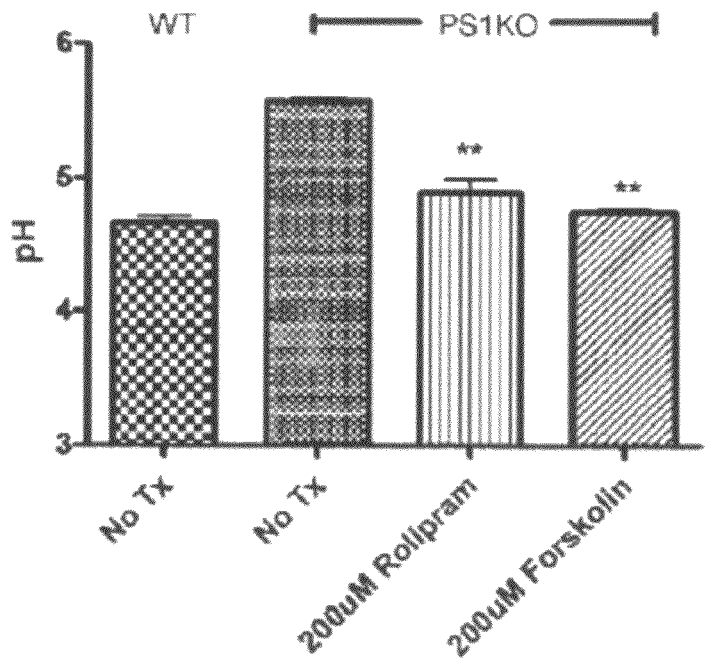

FIG. 10A shows that elevated lysosomal pH in PS1KO cells is restored to WT levels by the addition of the β-adrenergic agonists isoproterenol and clenbuterol, but remains unchanged by the addition of the β-adrenergic antagonist alprenolol and the α-adrenergic agonist phenylepherine. Treatment of PS1KO cells also restores CatB activity as determined by MR-CatB staining (see FIG. 10B), decreases LC3-II positive puncta (an indicator of autophagic dysfunction) (see FIG. 10C) restores turnover of the autophagy substrate P62 (see FIG. 10D) and decreases the number and load of autophagic vacuoles in the cells as determined by TEM (see FIG. 10E). Pretreatment with the PKA inhibitor H89, or the b-AR antagonist propranol both prevent the action of isoproterenol, demonstrating that b-AR binding and PKA activation are integral parts of the pathway leading to corrected lysosomal pH regulation. Moreover, addition of forskolin, an adenylate cylase inhibitor and rolipram, a PDE4 inhibitor both resulted in decreased lysosomal pH in PS1KO cells, further validating that the action of isoproterenol occurs via the canonical β-adrenergic pathway, ultimately leading to PKA activation.

Figure 11:
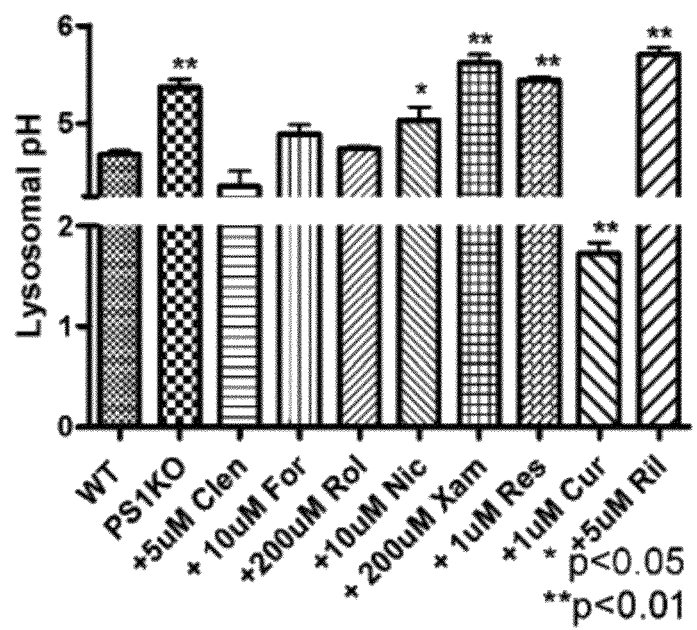
FIG. 11 depicts a histogram graph revealing the effects of multiple classes of compounds on restoring lysosomal pH in PS1KO blastocysts.

FIG. 11 shows the effects of multiple classes of compounds on restoring lysosomal pH in PS1KO blastocysts: PS1KO cells were treated with a variety of compounds, including β-adrenergic agonists (Clen, Xam), cAMP elevating compounds (For, Rol), Ca2+ pump inhibitors (Nic), at the indicated concentrations, followed by measurement of lysosomal pH. One way ANOVA analysis was performed with a Dunnet's Multiple Comparison Post-test to assess the significance in difference relative to WT pH. Therefore, since Clenbuterol, Forskolin, and Rolipram did not possess significant difference from WT lysosomal pH, they are categorized as effective at decreasing lysosomal pH to a level similar to that of WT cells. Abbreviations used are as follows, Clen=clenbuterol; For=forskolin; Rol=Rolipram; Nic=Nicardipine; Xam=xamoterol; Res=resveratrol; Cur=curcumin; Ril=Rilmenidine. It is important to note that dosage optimization, while established for toxicity, has not been optimized for lysosomal pH response, such that even those compounds not currently demonstrating an effect may do so with increased concentration, provided the dosage stays below the toxic threshold. Similarly, curcumin reduces lysosomal pH in excess of WT acidity, such that decreasing the dosage should allow for lysosomal acidification.

Further to the results presented in FIGS. 9-11, to identify which agents/drugs are the best candidates to be screened in vivo, we have formulated the following experimental strategy. Each drug produces a measurable response on several outcomes in PS1KO cells. These responses include restoration of lysosomal pH to a more acidic level, reduction of LC3-II punctae as visualized by ICC, and an increase in Cathepsin B activity. Additionally, a decrease in accumulated P62, an autophagy substrate, and a visible decrease in the build of AVs and autophagic intermediates serve as indicators for the efficacy of candidate agents/drugs. We will use a weighted sum of squares difference by calculating, for each drug, a score that measures the distance between the response of PS1 KO cells (y1, y2 ... yi) from the value in WT cells (x1, x2 ... xi) and multiplied by a weight (w1, w2 ... wi), determined to reflect the degree to which each outcome contributes to the potential value of the treatment: $\Sigma[(w1(y1-x1)/\sigma1)+(w2(y2-x2)/\sigma2) ... +(wi(yi-xi)/\sigma i)$, where $\sigma$ is the variance in WT cells. Agents or doses that cause cytotoxicity will be eliminated regardless of score. Drugs with the lowest score will be chosen for screening in vivo.

Methods to Evaluate Lysosomal Function and Reversal of Neurodegenerative Disease Lysosomal Dysfunction in Mouse Models In Vivo Testing of pH Modulating Agents:

Lysosomal pH is abnormal in PS FAD and may be abnormal in some APP models of AD. It will therefore be important to assess pH modulation in both PS/APP mice and Tg2576 mice, and possibly more aggressive APP models, to establish the ability of agents to prevent AD-related pathologies and behavioral deficits by administrating the drug chronically prior to onset of disease (3 months for PS/APP, 10 months for APP) and to reverse deficits after they appear (12 months in PS/APP and 18 months in APP). Clenbuterol and isoproterenol have been used mainly in models of ischemia and cardiac modeling [Rami et al. Neuroscience research, 2003. 47(4): 373-82; Soppa et al. Cardiovascular research, 2008. 77(4): 695-706; the contents of each of which is incorporated herein by reference in its entirety]. Both drugs cross the blood brain barrier (BBB) and will be delivered intraperitoneally (i.p.) to mice [Chi et al. Neurological research, 1998. 20(3): 259-64; Bakker et al. The American journal of physiology, 1998. 274(6 Pt 1): C1718-26; the contents of each of which is incorporated herein by reference in its entirety]. To determine optimal dose and treatment duration, mice will be injected I.P (0.25-2 mg/kg daily for 1 day up to 2 weeks) [Rami et al. Neuroscience research, 2003. 47(4): 373-82; Soppa et al. Cardiovascular research, 2008. 77(4): 695-706; Culmsee et al. European journal of pharmacology, 2007. 575(1-3): 57-65; Hon et al. Biological & pharmaceutical bulletin, 2011. 34(1): 61-5; Punithavathi et al. Journal of biochemical and molecular toxicology, 2010. 24(5): 303-12; the contents of each of which is incorporated herein by reference in its entirety] and changes in respiration, heart rate, blood pressure monitored as evidence of peripheral action [Kramer. Methods Mol Med, 2005.108: 51-62; Murphy, Respiratory Function Assays in Safety Pharmacology, in Drug Discovery and Evaluation, H. G. Vogel, Editor. 2006, Springer: New York. p. 141-8; the contents of each of which is incorporated herein by reference in its entirety].

We will also test for cardiac hypertrophy, the only major reported side effect of this drug class [Tan et al. Journal of cardiovascular pharmacology, 2003. 41(4): 518-25; the contents of which is incorporated herein by reference in its entirety], by monitoring heart weight [Murphy et al. Proceedings of the Society for Experimental Biology and Medicine. Society for Experimental Biology and Medicine, 1999. 221 (3): 184-7; the contents of which is incorporated herein by reference in its entirety] and will alter the dosing schedule or drug concentration, as needed. Efficacy in altering autophagic turnover of proteins will be evaluated by ICC and WB of autophagic substrates p62 and LC3 and by isolating lysosomes from brain and assessing changes in composition of substrates [Yang et al. Brain, 2011. 134(Pt 1): p. 258-77; the contents of which is incorporated herein by reference in its entirety].

In AD mouse models, efficacy will also be evaluated by assessing restoration of lysosomal size and reversal of: (a) intracellular and deposited Aβ; (b) axonal dystrophy and AV accumulations; (c) behavioral deficits, and (d) accumulation of autophagic substrates in brain and isolated AVs and lysosomes. This approach and all the techniques have been established and extensively validated in our recent evaluation of the effects of cystatin B deletion on these indices in TgCRND8 mice [Yang et al. Brain, 2011. 134(Pt 1): p. 258-77; the contents of which is incorporated herein by reference in its entirety]. Additionally, once the efficacy and mechanism of action for these drugs are established, we have access to mouse models that are null for the mucolipin-1 [Falardeau et al. BMC Genomics, 2002. 3(1): 3; the contents of which is incorporated herein by reference in its entirety] and C1C7 [Weinert et al. Science, 2010. 328(5984): 1401-3; the contents of which is incorporated herein by reference in its entirety] which would allow us to investigate whether the effects of the drugs are mitigated or mimicked by the introduction of these deletions.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A method for treating a subject with Alzheimer's Disease (AD), wherein the subject has impaired lysosomal activity, the method comprising providing a subject with AD and reduced lysosomal activity and administering to the subject an agent that enhances lysosomal activity, wherein the agent is a β-adrenergic agonist.

2. The method of claim 1, wherein the impaired lysosomal activity is determined by measuring elevated pH levels in lysosomes of the subject.

3. The method of claim 2, wherein the elevated pH level in lysosomes is equal to or greater than about 5.2.

4. The method of claim 2, wherein the impaired lysosomal activity is determined before, concurrently, or after the administering of the agent to the subject.

5. The method of claim 2, wherein the impaired lysosomal activity is determined before and/or after the administering of the agent to the subject.

6. The method of claim 1, wherein the impaired lysosomal activity is determined by detecting reduced levels of lysosomal protease activity in cells of the subject.

7. The method of claim 6, wherein the reduced levels of lysosomal protease activity in cells of the subject is reflected in reduced activity of at least three lysosomal proteases.

8. The method of claim 1, wherein the impaired lysosomal activity is determined using a sample isolated from the subject before and/or after the administering of the agent to the subject.

9. The method of claim 8, wherein the sample is cerebrospinal fluid isolated from the subject.

10. The method of claim 9, wherein the cerebrospinal fluid is lumbar cerebrospinal fluid.

11. The method of claim 1, wherein the agent is isoproterenol.

12. The method of claim 1, wherein the agent is clenbuterol.

13. The method of claim 1, wherein the subject is a mammal.

14. The method of claim 1, wherein the subject is a human.

15. The method of claim 1, wherein the subject has early onset familial AD.

* * * * *